United States Patent [19]
Green et al.

[11] Patent Number: 5,643,725
[45] Date of Patent: Jul. 1, 1997

[54] SEQUENCE AND ANALYSIS OF LKP PILIN STRUCTURAL GENES AND THE LKP PILI OPERON OF NONTYPABLE HAEMOPHILUS INFLUENZAE

[75] Inventors: Bruce A. Green, Pittsford, N.Y.; Charles C. Brinton, Jr., Export, Pa.

[73] Assignees: American Cyanamid Company, Wayne, N.J.; Bactex, Inc., Pittsburgh, Pa.

[21] Appl. No.: 277,231

[22] Filed: Jul. 19, 1994

[51] Int. Cl.$^6$ ............... C12Q 1/68; C07H 21/02; C07H 21/04; A61K 38/21
[52] U.S. Cl. ............... 435/6; 536/23.1; 536/24.3; 536/24.33; 536/23.7; 424/85.7; 514/2
[58] Field of Search ............... 435/6; 536/23.1, 536/24.3–0.33, 24.6; 424/88.7; 514/2

[56] References Cited

U.S. PATENT DOCUMENTS 5,336,490  8/1994  Brinton, Jr. et al. ............... 424/242.1

FOREIGN PATENT DOCUMENTS

93/19090  9/1993  WIPO.

OTHER PUBLICATIONS

Watson, Wendy, J. et al., "Identification of a Gene Essential for Piliation in *Haemophilus influenzae* Type b with Homology to the Pilus Assembly Platform Genes of Gram–Negative Bacteria" *Infection and Immunity* 62(2):468–475 (1994).

van Ham, S. Marieke et al., "Phase Variation of H. influenzae Fimbriae: Transcriptional Control of Two Divergent Genes through a Variable Combined Promoter Region," *Cell* 73:1187–1196 (1993).

van Ham, S. Marieke et al., "Cloning and expression in *Escherichia coli* of *Haemophilus influenzae* fimbrial genes established adherence to oropharyngeal epithelial cells," *EMBO Journal* 8(11):3535–3540 (1989).

van Alphen, Loek et al., "Blocking of Fimbria–Mediated Adherence of *Haemophilus influenzae* by Sialyl Gangliosides," *Infection and Immunity* 59(12):4473–4477 (1991).

Strom, Mark S. et al., "A single bifunctional enzyme, PilD, catalyzes cleavage and N-methylation of proteins belonging to the type IV pilin family," *Proc. Natl. Acad. Sci. USA* 90:2404–2408 (1993).

St. Geme, Joseph W., III et al., "High–molecular–weight proteins of nontypable *Haemophilus influenzae* mediate attachment to human epithelial cells," *Proc. Natl. Acad. Sci. USA* 90:2875–2879 (1993).

Sinha, N.D. et al., "Polymer support oligonucleotide synthesis XVIII: use of β–cyanoethyl–N, N–dialkylamino–/N–morpholino phosphoramidite of deoxynucleosides for the synthesis of DNA fragments simplifying deprotection and isolation of the final product," *Nucleic Acids Research* 12(11):4539–4557 (1984).

Saiki, Randall, K. et al., "Primer–Directed Enzymatic Amplification of DNA with a Thermostable DNA Polymerase," *Science* 239:487–490 (1988).

Palmer, Katherine L. and Munson, Robert S., Jr. "Construction of chimaeric genes for mapping a surface–exposed epitope on the pilus of non–typable *Haemophilus influenzae* strain M37," *Molecular Microbiology* 6(18):2583–2588 (1992).

Musher, Daniel M. et al., "Pneumonia and Acute Febrile Tracheobronchitis Due to *Haemophilus influenzae*," *Annals of Internal Medicine* 99:444–450 (1983).

Miller, J.H. "Generalized Transduction; Use of P1 in Strain Construction," *Experiments in Molecular Genetics*, pp. 201–205 Cold Spring Harbor Laboratory, Cold Spring Harbor, NY (1972).

McCaman, Michael T. et al., "Genetics and Regulation of Peptidase N in *Escherichia coli* K–12," *Journal of Bacteriology* 152(2):848–854 (1982).

Laemmli, U.K., "Cleavage of Structural Proteins during the Assembly of the Head of Bacteriophage T4," *Nature* 227:680–685 (1970).

Karasic, Raymond B. et al., "Evaluation of pilus vaccines for prevention of experimental otitis media caused by nontypable *Haemophilus influenzae*," *Pediatr. Infect. Dis. J* 8(1):S062–S065 (1989).

Kar, Siddhartha et al., "Cloning and Expression in *Escherichia coli* of LKP Pilus Genes from a nontypeable *Haemophilus influenzae* Strain," *Infection and Immunity* 58(4):903–908 (1990).

Gilsdorf, J.R., "Cloning, Expression, and Sequence Analysis of the *Haemophilus influenzae* Type b Strain M43p+ Pilin Gene," *Infection and Immunity* 58(4):1065–1072 (1990).

Forney, Larry J. et al., "Comparison and Analysis of the Nucleotide Sequences of Pilin Genes from *Haemophilu influenzae* Type b Strains Eagan and M43," *Infection and Immunity* 59(6):1991–1996 (1991).

Coleman, Trey et al., "Molecular Cloning, Expression, and Sequence of the Pilin Gene from Nontypeable *Haemophilus influenzae* M37," *Infection and Immunity* 59(5):1716–1722 (1991).

Chang, Annie C.Y. and Cohen, Stanley N. "Construction and Characterization of Amplifiable Multicopy DNA Cloning Vehicles Derived from the P15A Cryptic Miniplasmid," *Journal of Bacteriology* 134(3):1141–1156 (1978).

Brinton, Charles C., Jr. et al., "Design and development of pilus vaccines for *Haemophilus influenzae* diseases," *Pediatr. Infect. Dis. J.* 8(1):S54–S61 (1989).

Bluestone, Charles D. and Klein, Jerome O., "Otitis Media with Effusion, Atelectasis, and Eustachian Tube Dysfunction," *Pediatric Otolaryngology* pp. 356–512 (1983).

(List continued on next page.)

*Primary Examiner*—W. Gary Jones
*Assistant Examiner*—Dianne Rees
*Attorney, Agent, or Firm*—Hamilton, Brook, Smith & Reynolds, P.C.

[57] ABSTRACT

The isolation and cloning of the structural gene, hifA, for the NTHi pili serotype 5 and the serotype 1 LKP operon, DNA molecules capable of hybridizing to the DNA sequences of the *Haemophilus influenzae* genome related to the serotype 1 LKP operon and DNA molecules which encode LKP proteins are described.

4 Claims, 1 Drawing Sheet

OTHER PUBLICATIONS

Haslam, David et al., "The Amino–Terminal Domain of the P–Pilus Adhesin Determines Receptor Specificity," *Journal of Cellular Biochemistry Suplement* 18A:47, Abstract B112 (1994).

Kar et al. Infection and Immunity 58: 903–908.

Watson, W.J., et al., "Identification of a Gene Essential for Piliation in *Haemophilus influenzae* Type b With Homology to the Pilus Assembly Platform Genes of Gram–Negative Bacteria," *Database EMBL/GenBank/DDBJ on Strand, ID=HIIFC, AC=U02932* (1994).

Smith, A.L., "hif B of H. Influenzae is a Member of the Chaperone Family," *Database EMBL/GenBank/DDBJ on Strand, ID=HIHIFB, AC=X66606* (1992).

VanHam, S.M., et al., "Cloning and Expression in *Escherichia Coli* of *Haemophilus influenzae* Fimbral Genes Established Adherence to Oropharyn–Geal Epithelial Cells," *EMBO J.*, 8:3535–3540 (1989).

Green, B.A., et al., "Sequence of LKP Serotype 5 hifa Gene," *Database EMBL/GenBank/DDBJ on Strand, ID=HII9795, AC=U19795* (1995).

Lindberg et al, "Gene Products Secifying Adhesion of Uropathogenic *E. Coli* are Minor Components of Pili," PNAS 83, 1891–1895, 1986.

van Ham et al, "The Fimbrial Gene Cluster of *Haeprophilus Influenzae* Type b" Molecular Microbiology, 13; 673–684, 1994, (Augf Not Paper Art) Just FYI.

Sambrook et al, Molecular Cloning; A Laboratory Manual, CSHLP –1989, 9.47–9.57.

Langer Mann and Wright, "Molecular Anelysis of the *Haemophilus influenzae* Type b Pilin Gene," Molecular Microbiolgy 4(2)221–230, 1990.

```
             *        10         20         30         40         50         60         70
             *         *          *          *          *          *          *          *
LKP1 hifA  MEQFIMKKTT TGSLILLAFA TNAADPQVST ETSGKVTFFG KVVENTCKVK TDSKNMSVVL NDVGKNHLKT
                      10         20         30         40         50         60         70
                       *          *          *          *          *          *          *
LKP4 hifA  .........  ....L..... ....G.-VQADIN. .......... .......... .EH..L.... ........S.S.
                      10         20          30         40         50          60         70
                       *          *           *          *          *           *          *
LKP5 hifA  .........  ....L..... ....G.VQAADPNP ..K......Y. .......... SGNRD..... ......A...SQ

*        80         90         100        110        120        130        140
             *         *          *           *          *          *          *          *
LKP1 hifA  KKDTAMPTPF TINLENCSTT TTTNNKPVAT KVGAYFYSWK NADENNEYTL KNTKSGNDAA QNVNIQTFDA
                      80         90          100        110        120        130
                       *          *           *          *          *          *
LKP4 hifA  .VN....... ...T.Q..DP. .ANGTANK.N. ........L. .V.KE.NF.. ..EQTTA.Y. T......LMES
                      80         90          100        110        120        130
                       *          *           *          *          *          *
LKP5 hifA  .GY....... ...T.G.NAN .G.--..K.N ........N ...KE.S... ......S.LT.T.K. D......I.QE

*        150        160         170        180        190        200        210
             *         *          *           *          *          *          *          *
LKP1 hifA  NGTDAIEVVG NGTTDFTHSN TNDVATQQTV NKNHISGKAT INGENNVKLH YIARYYATAQ AEAGKVESSV
                      150        160         170        180        190        200        210
                       *          *           *          *          *          *          *
LKP4 hifA  ...K..S... ...KE.E..M.T. N.G..LN..P .NT....STQ .........T ...LT.T.ELP. F..Q....NK .T...Q....
                      150        160         170        180        190        200
                       *          *           *          *          *          *
LKP5 hifA  ......G.AD KTID.....K. NGSTNSDKP- T......SATA L.NQGDIA.. ....Q....GM .S....GPT..

*
LKP1 hifA  DFQIAYE*
LKP4 hifA  ........
LKP5 hifA  ..P....
```

SEQUENCE AND ANALYSIS OF LKP PILIN STRUCTURAL GENES AND THE LKP PILI OPERON OF NONTYPABLE HAEMOPHILUS INFLUENZAE

BACKGROUND OF THE INVENTION

Nontypable *Haemophilus influenzae* (NTHi) are primarily noninvasive human respiratory tract pathogens. NTHi can reside in the respiratory tract as a commensal organism or give rise to local infections, including otitis media, bronchitis, sinusitis, and rarely, pneumonia (1, 12). Several potential adherence factors have been described for NTHi adherence to human cells, including four classes of fimbriae/pili and two high molecular weight proteins with similarity to the filamentous hemagglutinin of *Bordetella pertussis*. (16).

One class of NTHi pili/fimbriae has been widely studied. The long thick pili (LKP) family are hemagglutination positive and mediate attachment to human mucosal cells (2). LKP pili are expressed by both NTHi and *H. influenzae* type b (Hib). They have also been shown to be vaccine candidates for NTHi otitis media in the chinchilla model, conferring protection against challenge with NTHi strains bearing the homologous pili serotype (8). The LKP family has been divided into 14 different strain specific types based on reactivity to polyclonal antisera raised against the purified pili. Little cross reactivity among pilus serotypes has been observed (2). Hemagglutination of human erythrocytes is accomplished via binding to the AnWj blood group antigen while binding to epithelial cells involves a sialic acid containing lactosylceramide receptor (18). Operons LKP pilin structural genes have been cloned and sequenced by several groups (4, 5, 7, 19), but only the genes responsible for pili serotypes 1 and 4 have been identified.

SUMMARY OF THE INVENTION

The invention relates to the isolation and cloning of the structural gene, hifA, for the NTHi pili serotype 5 and the LKP operon, the sequence of which is set forth in Table 3, SEQ ID NO: 1. The invention relates to DNA molecules capable of hybridizing to the DNA sequences of the *Haemophilus influenzae* genome related to the pili. The invention further relates to a DNA molecule which encodes a pilus protein, particularly a tip adhesin protein. The DNA molecules of the invention can be used in a method for assaying a sample, such as a blood sample, for the presence of *Haemophilus influenzae* in the sample. Accordingly, the invention further relates to the use of the DNA molecules as a diagnostic tool.

The invention also relates to a recombinant *Haemophilus influenzae* pili protein, such as a tip adhesin protein. The protein can be employed in a method for immunizing an animal, such as a human, as a vaccine, therapeutic or diagnostic.

BRIEF DESCRIPTION OF THE DRAWING

The FIGURE is a graphic illustration of the conserved regions of the structural genes of H influenzae serotypes 1 (SEQ ID NO: 12), 4 (SEQ ID NO: 13) and 5 (SEQ ID NO: 14).

DETAILED DESCRIPTION OF THE INVENTION

The LKP pili are composed of repeating polymers of pilin subunits with molecular weights varying between 22,000 and 27,000 daltons. Three LKP pili components from Hib strains have been previously identified, the pilin structural gene encoded by hifA, a periplasmic chaperone designated hifB (7, 20) and a membrane anchor protein encoded by hifC (21). The hifB locus shows extensive homology to the papD gene of P pili of (*Escherichia coli*) also a periplasmic chaperone (20). The LKP 4 pilus operon cloned by van Ham et al. also contains a variable combined overlapping promoter region which is responsible for the observed phase variation of fimbrial expression in NTHi. The LKP operon has a relatively unique structure with the pilin structural gene, hifA, being transcribed in an opposite orientation to the periplasmic chaperone gene, hifB (20).

The cloning of the serotype 5 structural gene, and the sequence of the entire LKP 1 operon is described herein (SEQ ID NO: 1 as shown in Table 3). The operon is composed of five separate genes, designated hifA nt 1882-2532 of SEQ ID NO. 1, hifB nt 2854-3630 of SEQ ID NO.: 1, hifC nt 4016-6238 of SEQ ID NO.: 1, hifD nt 6259-6873 of SEQ ID NO.: 1 and hifE nt 6955-8265 of SEQ ID NO.: 1, the deduced amino acid sequences are SEQ ID NOs.: 2–6, respectively. From sequence homology to the pap operon of *E. coli*, the identities of the remaining genes are: hifC, membrane anchor; hifD, tip associated protein; and hifE, tip adhesin protein. Serotype 1 and serotype 4 pili have also been expressed using the LKP 1 operon and the LKP 4 structural gene, showing that serotype specificity resides primarily in the pilin structural genes.

A DNA molecule of the invention is capable of hybridizing to the DNA sequences of the *Haemophilus influenzae* genome related to the pili. The DNA molecule preferably contains at least about 400 nucleotides, more preferably at least about 1000 nucleotides, and most preferably at least about 1200 nucleotides. The DNA molecule preferably shares at least about 70% homology or the corresponding sequences of the *Haemophilus influenzae* genome, more preferably at least about 80% and most preferably at least about 90%.

The DNA molecule of the present invention is, preferably, capable of hybridizing to serotype conserved regions of the *Haemophilus influenzae* genome. A particularly preferred embodiment is the region encoding the tip adhesin protein (hifE). For example, the DNA molecule can be capable of hybridizing to the gene encoding the tip adhesin protein of serotype 1, preferably the sequence set forth between about nucleotide 6955 to 8265 of SEQ ID NO:1. In one embodiment, the DNA molecule is capable of hybridizing to the genome under stringent conditions.

In one embodiment, the DNA molecule can be at least about 400 nucleotides of a serotype conserved region of the genome, such as the sequences encoding a tip adhesin protein, such as that of serotype 1. For example, the DNA molecule can be a DNA molecule of at least about 400 nucleotides between about nucleotide 7000 to 7400 of SEQ ID NO:1.

In another embodiment, the *Haemophilus influenzas* serotype 1 LKP tip adhesin protein can be used in methods of vaccinating a mammal against *Haemophilus influenzas*. Testing the efficacy of proteins as Vaccines is well known to those of skill in the art. For example, Brinton, C. C. et al. ("Design and development of pilus vaccines for *Haemophilus influenzae* diseases," *Pediatr. Infect. Dis. J.*, 8 Suppl.:54–61 (1989)), and Karasic, R. et al., ("Evaluation of pilus vaccines for prevention of experimental otitis media caused by nontypable Haemophilus influenzas," *Pediatr. Infect. Dis. J.*, 8 Suppl.:62–65 (1989)) teach general methods of administering *Haemophilus influenzas* protein to animals to provide active and passive immunity against *Haemophilus influenzae* infection.

*H. influenzas* serotype 1 LKP tip adhesin proteins can be purified and characterized using standard techniques such as described in Brinton, et al. and Karasic, et al. For example, tip adhesin protein call be produced and purified to remove trace amounts of copurifying contaminants and lipopolysaccharide. The resulting tip adhesin preparation can be characterized by electrophoresis on a polyacrylamide gel/sodium dodecyl sulfate gel and further evaluated for its ability to adhere to human erythrocytes and buccal cells and to induce antibodies. Electron microscopy can also be used to detect the presence of particulate impurities and contamination. Purity and homogeneity of the tip adhesin preparation can be tested by scanning ultraviolet absorption (from 350 to 250 nm). Typing sera can be obtained by immunization of rabbits with purified (not hyperpurified) pili, and the resulting antisera can be used to determine the degree of crossreactivity between serotypes. Bacterial cell agglutination can be used to screen *H. influenzae* disease isolates.

In addition, using an art-recognized in vivo model using chinchillas, the purified tip adhesin protein preparation can be evaluated as a vaccine in order to prevent otitis media due to nontypable *H. influenzae* infection. For example, active immunization using an intrabullar challenge model can be evaluated by providing animals in the vaccine group with an intramuscular dose of vaccine preparation containing *H. influenzae* tip adhesin protein, followed by a booster dose 28 days later. Control animals can receive two injections of saline placebo 28 days apart. Ten days after the second dose of vaccine or placebo, all chinchillas can be challenged by inoculation with 10 colony-forming units (cfu) of *H. influenzae* (either the homologous strain or a heterologous strain) through the epitympanic bulla.

The efficacy of passive immunization with *H. influenzae* tip adhesin protein can also be evaluated. High titer antiserum can be produced by immunizing rabbits with purified LKP tip adhesin. Three groups of chinchillas can be inoculated intraperitoneally (1 ml) with different dilutions of antiserum; undiluted; 1:10 dilution or 1:100 dilution control animals are inoculated intraperitoneally with 1 ml undiluted nonimmune rabbit serum. One day later, all chinchillas are challenged (right intrabullar) with 10 cfu of homologous *H. influenzae.*

The efficacy of active immunization on nasopharyngeal colonization with *H. influenzae* can also be evaluated. For example, chinchillas in the vaccine group can receive two 100 μg doses of LKP tip adhesin protein, 28 days apart, and controls can be given two doses of placebo. Ten days after the second dose, all chinchillas are inoculated with 107 cfu of *H. influenzae.* One day after bacterial inoculation, continuous negative pressure(−40 cm $H_2O$) is applied for 5 minutes to the middle ears of all animals through a needle inserted into the bullae. The animals are examined every 3–4 days for approximately 2 weeks. Cultures can be obtained from the middle ear through the bulla, and the presence of middle ear effusion determined by otomicroscopy, tympanometry and direct intrabullar examination. Serum antibody titers against pili can be measured by piliated cell agglutination.

Thus, a *H. influenzae* LKP tip adhesin protein vaccine can be produced and evaluated for efficacy in immunizing a mammal against *H. influenzae* infection.

EXEMPLIFICATION

Bacterial strains and plasmids.

NTHi strains P860295 (ATCC 53775), P861249 (ATCC 53778), and 00P810384 (ATCC 53779) which express LKP serotypes 1,4, and 5 respectively, described previously (2) were employed. *E. coli* strains MB392 (7) and HB101 were used as hosts for recombinant plasmids and strain DH5-α was used for cloning steps involving β-galactosidase α-peptide complementation. NTHi were grown in brain heart infusion (Difco Laboratories, Detroit, Mich.) containing 10 μg/ml hemin (Sigma Chemical Co., St. Louis, Miss.) and 2 μg/ml NAD (Sigma) at 37° C. *E. coli* strains were grown in Luria broth (11) at 37° C. Where appropriate, antibiotics were used at the following concentrations: ampicillin (Sigma) 100 μg/ml, kanamycin (Sigma) 25 μg/ml, and chloramphenicol (Sigma) 20 μg/ml.

Construction and properties of plasmid pHF1 which expresses LKP1 pili in *E. coli* as described previously (7) were employed. Plasmid pPX551 is a pUC18 derivative containing the 1.9 kb XhoI fragment of pHF1 inserted into the BamHI site. Deletion clones of pHF1 lacking the pepN locus were constructed as described in the text. The LKP 1 pilin structural gene was isolated by PCR amplification of P860295 chromosomal DNA using primers with the following sequences: for the 5' end of the gene-5'GTGCTGGATCgGTTTCTCTTGCATTACATTAGG 3' (SEQ ID NO:8) and for the 3' end- 5'TTAGGAATTCGGAAGCGTTTTTTACTTTTTTTGG3' (SEQ ID NO:9). The 5' primer included a HindIII restriction site, underlined in the sequence, and the 3' primer included an EcoRI site also shown underlined. The PCR product was cloned into pCR1000 (Invitrogen, Inc., Calif.) as per manufacturers directions. The LKP 4 structural gene was subcloned by blunting the EcoRI site with Klenow in the presence of all four dNTPs, and cutting with Asp718 I (an Asp718 I site is located in the vector) releasing the fragment. The LKP 4 gene was ligated into HindII-Asp718 I cut pPX191 ( a derivative of pUC19 with the bla gene replaced by the cat gene from pACYC184 (3)) to form pPX602. The LKP 5 pilin structural gene was isolated from P810384 by PCR using the following primers: for the 5'end-5'-AACGAATTCTGCTGTTTATTAAGGCTTTAG (SEQ ID NO:10) and for the 3'-AGCTGGATCCTTGTAGGGTGGGCGTAAGCC (SEQ ID NO:11). The PCR product of approximately 1 kb was cloned into pCRII (Invitrogen, Inc., San Diego, Calif. and subcloned as a blunt ended fragment by Klenow treatment of EcoRI ends generated using the vector's flanking EcoRI sites. The LKP 5 pilin gene was subcloned into plasmid pPX191 and orientation determined by restriction analysis. The LKP 5 subclone was saved as pPX605.

Oligonucleotide synthesis.

The synthetic oligonucleotides used as primers for PCR amplification and DNA sequencing were synthesized on an Applied Biosystems (ABI) 380B DNA synthesizer using b-cyanoethyl phosphoramidite chemistry (15).

Polymerase chain reaction (PCR) amplification.

The LKP 4 hifA and LKP 5 hifA pilin genes were amplified by PCR from NTHi strains P861249 and P81034 respectively, using standard PCR amplification protocols (14) .

DNA sequencing.

The hifA gene contained on plasmid pPX551 and the entire LKP 1 operon contained on plasmid pHF1 were sequenced with standard M13 sequencing primers and with overlapping sense and antisense primers. All the DNA sequencing was done on an Applied Biosystems (ABI).

373A DNA Sequencer, utilizing the Taq thermal cycling DyeDeoxy™ Terminator sequencing kit from ABI, part #901497. The LKP 4 and LKP 5 serotypes were sequenced directly from the PCR products using the PCR amplification primers and internal synthetic primers based on the LKP 1 sequencing study.

SDS-PAGE analysis.

Sodium dodecyl sulfate polyacrylamide gel electrophoresis (SDS-PAGE) was performed in a 70 by 100 mm mini-gel system (Bio-Rad, Richmond, Calif.) using the method of Laemmli (9). Samples were reduced with β-mercaptoethanol or DTT in sample preparation buffer and boiled for 5 min. Gels were run at 150 V constant voltage. Separated proteins were detected by staining with Coomassie brilliant blue G-250 (Sigma).

Partial purification of pili.

LKP pili were purified according to previously described methods using differential pH solubility (2). Briefly, piliated bacteria were harvested from liquid culture by centrifugation and washed 2× in phosphate buffered saline, pH 7.2. The bacterial pellet was resuspended in 100 mM tris, pH 10.3, containing 150 mM NaCl at a ratio of 4 ml buffer/g wet weight of cells. Pili were sheared off of the cells by blending in an Oster miniblender for three 3 min bursts at 4° C. Bacterial debris was separated by centrifugation and discarded. The supernatant was dialyzed against 50 mM NaAcetate, pH 5.0 overnight to precipitate pili and denature other proteins. The pellet was collected by centrifugation at 15,000×g at 4° C. and dissolved overnight in 50 ml of 0.01M CAPS buffer, pH 10.4 with gentle rocking. This cycle of acid precipitation and solubilization in basic buffer was repeated two more times. The final acid pellet was then resolubilized in 0.01M NaPhosphate, pH 10.4 and non soluble material discarded. This soluble fraction was referred to as partially purified pili.

Sequence of the LKP 1 operon.

The LKP 1 operon was sequenced as described above and the full sequence is set forth in SEQ ID NO:1 Table 3. The LKP 1 operon shows a structure similar to that reported by van Ham (20) for the LKP 4 operon, with overlapping divergent promoters controlling the pilin structural gene and the rest of the operon. Altogether, sequence analysis identified six potential open reading frames (ORFs) in the LKP operon, including the hifA and hifB genes. The remaining potential ORFs in the LKP1 operon were identified by alignment of the deduced amino acid sequence of each reading frame with translation products from Entrez Sequences Database Release 10.0 of the National Center for Biotechnology Information (National Library of Medicine, Bethesda, Md.) as noted above. The DNA sequence of the ORFs had good homology with both the pap locus and the fim gene cluster of E. coli and the mrk locus of Klebsiella pneumoniae. Derived amino acid sequences of the ORFs are also shown in DNA SEQ ID NO:1. When these sequences were aligned to Entrez Sequences, each ORF had a high degree of homology to a corresponding gene in the mrk pili operon of Klebsiella pneumoniae. A function for each reading frame was also assigned based on this analysis. There are five ORFs which appear to be grouped into an operon controlled by the hifB promoter region. After the hifB (periplasmic chaperone SEQ ID NO:3) gene, the second reading frame hifC was designated, a membrane anchor protein SEQ ID NO:4, the third ORF hifD was designated, a tip associated protein SEQ ID NO: 5, and the fourth ORF hifE was designated, a tip adhesin protein SEQ ID NO:6. The functions of the various open, reading frames are shown below the derived amino acid sequences in SEQ ID NO:1.

The pilin gene (hifA) and the periplasmic chaperone gene (hifB) are transcribed in opposite orientations as in the LKP 4 operon with the promoter region having the previously identified (20) TA repeats. Since pHF1 expresses LKP1 pili in E. coli, there are 10 TA repeats in the intrapromoter region as described by van Ham et al. (20). These TA repeats are responsible for phase variation of the LKP pili phenotype, with loss of some of the repeats resulting in loss of piliation and a TA repeat number between 10 or 11 allowing expression of the LKP operon.

The predicted size of the LKP 1 hifA gene product is approximately 21.2 kilodaltons, assuming a signal sequence length of 20 amino acids as has been described for the M43 pilin of Hib(6) while the observed molecular weight in SDS-PAGE gels is approximately 27 kilodaltons. Part of this may be explained by the anomalous sequence migration of LKP pilins in general in SDS-PAGE gels (mature LKP 4 migrates at a molecular size of 24 kilodaltons while its predicted size is 22.1 kilodaltons) but the exact explanation remains unknown.

Sequence comparison of LKP serotypes 1, 4, and 5 hifA genes.

This report represents the first sequence analysis of the hifA genes encoding LKP serotypes 1 and 5. The hifA gene from an LKP 4 expressing Hib strain has also been sequenced (19) and the derived amino acid sequence shows 99% identity with the LKP 4 hifA derived amino acid sequence contained herein. The hifA gene sequences from Hib strains Eagan (serotypes) and M43 have been published (5). The LKP 1 hifA gene should encode a protein of approximately 21.5 kD while the predicted molecular weight of the LKP 4 hifA protein is 23.8 kD. The actual hifA gene products observed in recombinant E. coli are of approximately the correct sizes in Western blots for LKP 4 and 5, but the LKP 1 pilin runs aberrantly at a higher molecular weight than predicted at 26 kD. The derived amino acid sequences were aligned using MacVector software and show a very high degree of homology throughout most of their length with LKP 4 hifA and LKP 5 hifA proteins being 70 and 67% identical to LKP 1 hifA, respectively. The alignment between the sequences is very good at the amino termini of the proteins, with three major areas of sequence divergence in the LKP 1, 4, and 5 serotype genes farther into the proteins as shown in the FIGURE. Since little cross reactivity is observed between anti-LKP1, anti-LKP4, or anti-LKP 5 sera with intact pili of a heterologous serotype, the sequences responsible for the serotype specificity of the typing antisera must be located in these regions. By comparison of the sequences in GenBank to the LKP 4 sequence, the H. influenzae type b M43 pilin (6) sequenced by Gilsdorf et al. also appears to be an LKP 4 serotype gene (data not shown).

Cloning of hifA genes encoding other LKP serotypes.

HifA loci encoding serotype 4 and serotype 1 LKP genes have been described (7, 19). To determine if the serotype specificity of LKP pili is located within the hifA gene, PCR was used to clone the serotypes 4 and 5 pilin genes from an NTHi strains expressing these pili. The PCR product for the LKP 4 pilin gene was cloned into pPX191 as described above and is expressed under control of the lac promoter. The hifA gene from an LKP 5 expressing NTHi strain was isolated by PCR as described and cloned into pPX191 for expression under lac control.

Assay Probe Construction:

An approximately 1100 bp fragment from plasmid pHF1 (which contains the LKP 1 serotype operon) was amplified by PCR using primers which hybridize at the 5' and 3' ends of the hifE gene. This gene encodes the putative tip adhesin protein of the LKP 1 pili as described in the manuscript. The PCR reaction included digoxigenin labeled dUTP along with the four dNTPs to label the PCR reaction product with digoxigenin. This probe was electrophoresed on an agarose gel and purified by cutting out the ~1.2 kb band and extracting the DNA by standard methods. The probe was redissolved in 30 μl of appropriate buffer.

Hybridization Assay for *Haemophilus influenzae*

Eleven randomly chosen *Haemophilus influenzae* clinical isolates were grown on BHI-XV plates at 37° C. with 5% $CO_2$ and also streaked onto BHI agar. All isolates grew only on the BHI-XV plate, indicating that they were *H. influenzae*. The isolates included 2 Hib strains and 9 NTHi. The strains were inoculated onto a nylon membrane placed onto BHI-XV agar. Five clinical isolates of another respiratory pathogen, *Moraxella catarrhalis* were also spotted onto the filter. The bacteria were grown overnight at 37° C. in 5% $CO_2$. After growth, 2 *Bordetella pertussis* strains were spotted onto the filter. Filters were processed for colony hybridization according to the method of Maniatis et al. (*Molecular Cloning: A Laboratory Manual*, 1991, Cold Spring Harbor Laboratories, Cold Spring Harbor, N.Y.). Filters were blocked in pre-hybridization solution as described by Boehringer-Mannheim for the Genius™ system at 65° C. for 3 hours. Colony debris was removed by gentle rubbing with wet paper towels. The probe, 30 μl, was added to 5 ml of pre-hybridization solution and boiled for 10 minutes to denature the DNA. Probe was immediately added to the filter and allowed to hybridize overnight at 65° C. Filter was washed in 2× SSC, 0.1% SDS, 2× for 5 min/wash at room temperature followed by 2, 15 minute washes with 0.2× SSC, 0.1% SDS at 65° C. Bound probe was detected using alkaline phosphatase labeled anti-digoxigenin antibodies as described by the manufacturer.

TABLE 1

HYBRIDIZATION OF dig-LABELED LKP 1 TIP PROBE TO RANDOM CLINICAL ISOLATES

| Bacterial Strain | Number of Positive Results | | | # Total |
|---|---|---|---|---|
| | Strong Signal | Weak Signal | No Signal | |
| *H. influenzae* | 4 | 4 | 3 | 11 |
| *M. catarrhalis* | 0 | 0 | 5 | 5 |
| *B. pertussis* | 0 | 0 | 0 | 2 |

The probe was specific for *H. influenzae* with no hybridization seen with either *M. catarrhalis* or *B. pertussis*. However, only 8 of the *H. influenzae* strains gave detectable signals. It is possible that the *H. influenzae* strains could have lost the LKP operon during laboratory passage and would thus not react with the probe.

Hybridization Assay of Non-Typable Strains of *Haemophilus influenza* pili

Ten LKP pili expressing NTHi strains which express differing serotypes of LKP pili, along with Hib Eagan (known to express LKP serotype 3) were grown on a nylon filter overlayed onto chocolate agar at 37° C. in 5% $CO_2$. An additional NTHi isolate was also included. After growth, two strains appeared yellow on the filter which was suggestive of non-Haemophilus bacteria, so they were tested by growth on BHI and BHI-XV. This experiment showed them to be contaminants and not NTHi. The filter was removed from the agar and processed as described above. The probe from the first experiment was reboiled and added to the filter as before, except that the hybridization temperature was lowered to 62° C. The filter was washed as before except that the wash temperature was also 62° C. Bound probe was detected as above.

TABLE 2

HYBRIDIZATION OF dig-LABELED TKP TIP PROBE TO LKP TYPE STRAINS

| LKP Serotype | Signal with probe | No signal with probe | ID of strain |
|---|---|---|---|
| 5 | Strong | | NTHi |
| 2 | Moderate | | NTHi |
| 9 | Strong | | NTHi |
| 1 | Strong | | NTHi |
| 6 | Moderate | | NTHi |
| 13 | Strong | | NTHi |
| 4 | Strong | | NTHi |
| 7 | Moderate | | NTHi |
| | | X | Contaminant |
| | | X | Contaminant |
| 10 | Weak | | NTHi |
| 4 | Strong | | Hib |

The results set forth above establish that the DNA probes hybridized selectively to *Haemophilus influenzae*.

Equivalents

Those skilled in the art will recognize, or be able to ascertain using not more than routine experimentation, many equivalents to the specific embodiments of the invention described herein. Such equivalents are intended to be encompassed by the following claims.

1. Bluestone, C. D., and J. O. Klein. 1983. "Otitis media with effusion, atelectasis, and eustachian tube dysfunction." In *Pediatric Otolaryngology.*, 356. Bluestone and Stool ed. W. B. Saunders Co. Philadelphia.

2. Brinton, C. C., Jr., M. J. Carter, D. B. Derber, S. Kar, J. A. Kramarik, A. C. C. To, and S. W. Wood. 1989. "Design and development of pilus vaccines for *Haemophulus influenzae* diseases." *Pediatr. Infect. Dis. J.* 8 Suppl.: 54–61.

3. Chang, A. C. Y., and S. N. Cohen. 1978. "Construction and characterization of amplifiable multicopy DNA cloning vehicles derived from the p15A cryptic miniplasmid." *J. Bacteriol.* 134: 1141–1156.

4. Coleman, T., S. Grass, and R. Munson Jr. 1991. "Molecular cloning, expression, and sequence of the pilin gene from nontypeable *Haemophilus influenzae* M37." *Infect. Immun.* 59: 1716–1722.

5. Forney, L. J., C. F. Marrs, S. L. Bektesh, and J. R. Gilsdorf. 1991. "Comparison and analysis of the nucleotide sequences of pilin genes from *Haemophilus influenzae* type b strains Eagan and M43." *Infect. Immun.* 59: 1991–1996.

6. Gilsdorf, J. R., C. F. Marrs, K. W. McCrea, and L. J. Fornay. 1990. "Cloning, expression, and sequence analysis of the *Haemophilus influenzae* type be strain M43p+ pilin gene." *Infect. Immun.* 58: 1065–1072.

7. Kar, S., S. C. -M. To, and C. C. Brinton Jr. 1990. "Cloning and expression in *Escherichia coli* of LKP pilus genes from a nontypeable *Haemophilus influenzae* strain." *Infect. Immun.* 58: 903–908.

8. Karasic, R., D. J. Beste, S. C. -M. To, W. J. Doyle, S. J. Wood, M. J. Carter, A. C. C. To, K. Tanpowpong, C. D. Bluestone, and C. C. Brinton Jr. 1988. "Evaluation of pilus vaccines for prevention of experimental otitis media caused by nontypable *Haemophilus influenzae.*" *Pediatr. Infect. Dis. J.* 8 (Suppl.): S62–65.

9. Laemmli, U. K. 1970. "Cleavage of structural proteins during the assembly of the head of bacteriophage T4." *Nature* (London) 227: 680–685.

10. McCaman, M. T., A. McPartland, and M. R. Villarejo. 1982. "Genetics and regulation of peptidase N in *Escherichia coli* K-12." *J. Bacteriol.* 152: 848–854.

11. Miller, J. H. 1972. In Experiments in molecular genetics., 203. Cold Spring Harbor Laboratory. Cold Spring Harbor, N.Y.

12. Musher, D. M., K. R. Kubitshek, J. Crennan, and R. E. Baughn. 1983. "Pneumonia and acute febrile tracheobronchitis due to *Haemophilus influenzae*." *Ann. Intern. Med.* 99: 344-350.

13. Palmer, K. L., and R. S. Munson Jr. 1992. "Construction of chimeric genes for mapping a surface-exposed epitope on the pilus of non-typable *Haemophilus influenzae* strain M37." *Mol. Microbiol.* 6: 2583-2588.

14. Saiki, R. K., D. H. Gelfand, S. Stoffel, S. J. Scharf, R. Higuchi, G. T. Horn, K. B. Mullis, and H. A. Erlich. 1988. "Primer-directed enzymatic amplification of DNA with a thermostable DNA polymerase." *Science* 239: 487-491.

15. Sinha, N. D., J. Biernat, J. McManus, and H. Koster. 1984. "Polymer support oligonucleotide synthesis XVIII: use of b-cyanoethyl-N, N-dialkylamino-/N-morpholino phosphoramidite of deoxynucleosides for the synthesis of DNA fragments simplifying deprotection and isolation of the final product." *Nucleic Acids Research* 12: 4539-4557.

16. St. Geme, J. W., III, S. Falkow, and S. J. Berenkamp. 1993. "High-molecular-weight proteins of nontypable *Haemophilus influenzae* mediate attachment to human epithelial cells." *Proc. Natl. Acad. Sci. USA* 90: 2875-2879.

17. Strom, M. S., D. N. Nunn, and S. Lory. 1993. "A single bifunctional enzyme, PilD, catalyzes cleavage and N-Methylation of proteins belonging to the Type-IV pilin family." *Proc Natl Acad Sci USA* 90: 2404-2408.

18. van Alphen, L., L. Geelan van den Broek, L. Blaas, M. van Ham, and J. Dankerr. 1991. "Blocking of fimbria-mediated adherence of *Haemophilus influenzae* by sialyl gangliosides." *Infect. Immun.* 69: 4473-4477.

19. van Ham, S. M., F. R. Mooi, M. G. Sindunata, W. R. Maris, and L. van Alphen. 1989. "Cloning and expression in *Escherichia coli* of *Haemophilus influenzae* fimbrial genes establishes adherence to oropharyngeal epithelial cells." *EMBO Jour.* 8: 3535-3540.

20. van Ham, S. M., L. van Alphen, F. R. Mooi, and J. P. M. van Putten. 1993. "Phase variation of *H. influenzae* fimbriae: Transcriptional control of two divergent genes through a variable combined promoter region." *Cell* 73 1187-1196.

21. Watson, W. J., J. R. Gilsdorf, M. A. Tucci, K. W. McCrea, L. J. Forney, and C. F. Marrs. 1994. "identification of a gene essential for piliation in *Haemophilus influenzae* type b with homology to the pilus assembly platform tenes of gram-negative bacteria." *Infect. Immun.* 62: 468-475.

TABLE 3

```
AAGCTTGCATGCCTGCAGGTCGACTCTAGAGGATCATTCCATTGTGTTTAATTCTTTAATAAACACCAAGGTGAGGTAGAAATATTCAGTTCATC
AAGCAAGGATTTTTGCGTAAAACGATCGGCTAATAATCAAATACATGTTGATTAACGAAGTTTTATGATTGCTGAGTAATTCAGTCAAAGGCG
TTTTTTCCAGCGTTCAATTTCCGCCGTGATGATCGCATTTTCAGGTAAGTCAAAAACTGGCGACATAAAACGTTCAAGGGTTCAACATAAATATCT
AAAGGTGCACCAGCGTAACCTAACATTCTGCCGAGTTGTCCGTTGCCGAGAACATAAACGGTTGGGTATAAGGTGGAGTTTTGCATAATATTCT
CGTTAAATTTACGAAAAAAACACCGTCACTTTAAAAGTGCGGTCAGATCTGAAGATATTTTTAGTGCGTGGATCGGATGGGATGTCCAGTACAGCACG
AGTTTGGCTTTCACGGAAGAATTGCAAGCGTGAAAGCAATTCTGCAATTCTGAAAGCAATTTCGGGCGTGCTAACAACCCAGCATTTGCCGCGC
CTGCAGAGCCAATGCTAATGTCCGACTGGAATCCCTTTGGCATTTGCACAATTTGAATTAAAGGCTATCCACACCACTTAACATAGAACTTTT
ACTGGCACCCCCAGCACTGGCACAAGTGTTTTGGCGTGCGATCATACCAGGTAAATGTCCGCACCGCTGCACCAGCAATAATTACTTTTATAGCC
ATTTTTTTGTGCATTTTCGGCAATTTCGAAAAGTTTATCAGGCTACGATGGGCAGAGACGACTTCCACATGATAAGGCACGTTTAATTCATCTA
AAATCTGAGTTGCCTCTTGCATAGTAGCCCAATCACTTTTGACCCCATCACAACGGCAATTTGTCAGTTTGACATGCTATTTTCTCAATTT
TCTAATTTAAAAACGTGGTTGTAGAATAGCATAGATATCGAGCAAACGTTGCTATTTATGTACGTATTAATGGGGGATATTTTATAATT
ATTTGATTTTTAAATTTTATGATAACTATACTTGATACCAAATTGATAATGGGGCGATAGTTTATATGGGACTAGAACTGAAAATTATTAGATAAGCTCGCA
CAATCAAAATCTACATTTAATTGAATGAATTAGTTTCTTTGTTAGCTCAACAAGGTTATGAAAAGCGAGAAATGGCAGGTTCTCGAGTGAGATT
TTATAATAGAACACTCGAACATATGATTGTTGTTACCAAGCCTCATCCTGAAATTATATATAAAGGCGGTGTTTAAAGTCAGTGAAAGAATCAT
TAAACAGGTAGGTATTCTATGAAGTTATTAATTTATAAAGGTATGTTGCACGATTGAGGCCGATTGAGAAAAGAATTTCATCAATCTGTTGATTTATATTTGGCAAAC
TTGCTTACATTCGTGATTTAGTGACTTACGAAGCAGAGATCATTATCGAGTTAGAAAAAGAATTTCATCAATCTGTTGATTTATATTTACAAGAT
TGTTTGGAATTAGGTAAAGAACCGAATAAGCCTTTTAAAGGTGTATTTAATGTACGAATTGGCGAGGAATTGCATAGAGAAGCAACGATCATAGC
TGGCGATCGTTCTCTAATGCTTTTGTGACGGAAGCAATGCCCATGTAGAGACATATAACAAACGCTGGGCTTAGATTTGTAGGCGTAAGCTCACGTGGATACATATAAAA
TTTTTTCATCACGTAGGCTGGGCGTAAGCCCATGGGCGTAAGCCCAGAGATATAACAAACGCTGGGCTTAGATTGCATTACATTAGTGTAATTTCACATTTCGTAAGCAATTGC  AA
AGATTTGTAGGGTGGGCGTAAGCCCACGGCGTAAGCCCAGAGATATAACAAACGCTGGGCTTAGATTGCATTACATTAGTGTAATTTCACATT▼GluTyr Ala Ile Gln Phe  A
TCAACTGAGGAATTCTACTTTACCAGCTTCCGCTTGACGTGTTGCATAGTATCTAGCGATATAGTGTAATTTCACATTGTAATTTCACCGTTAATTGT  A
sp Val Ser Ser Glu Val Lys Gly Ala Glu Ala Thr Arg Tyr Ala Ile Tyr His Tyr Arg Ala Ile Tyr His Leu Lys Val Asn Asn Glu Gly Asn Ile  Thr
  AGCTTTTCCTGAAATATGATTTTATTCACAGTTGTTGTGCAACGTCAGTTGTTGCATCATTTGTATTGCTATGCTATGCTACAATCGTTGTCCGTTGCCG   AA
Ala Lys Gly Ser Ile  His Asn Lys Asn Val Thr Gln Gln Thr Ala Val Asp Asn Ser His Thr Phe Asp Thr Phe Asp Thr Phe Gly Asn Gly Val  Va
CTTCAATTGCATCTGTACCATTAGCATCCAAAAAGCTGAATAAGCTCCAACTTTTGTTGCAACAGGCTTATATTAGTAGTAGTAGAACAATTTC
l Glu Ile  Ala Asp Thr Gly Asn Ala Asp Phe Leu Gln Ile  Asn Val Asn Gln Ala Ala Asp Asn Gly Ser Lys Thr Asn Gly Ser Lys Thr Lys Thr Tyr Glu A
TTATTTTCATCTGCATTTTCCAAGAATAGAAATAAGCTCCAACTTTTGTTGCAACAGGCTTATATTAGTAGTAGTAGAACAATTTC
sn Asn Glu Asp Ala Asn Lys Trp Ser Tyr Phe Tyr Ala Gly Val Lys Thr Ala Gly Val Pro Lys Asn Asn Thr Thr Thr Ser Cys Asn Glu
TAAATTAATTGTAAAGGTGTTTGGCATCGCTGTATCTTTTTTAGTTTTTTAAATGATTTTTAAATGATTTTTACCCACATCATTAATTACTACGCTCATATTTTAC
Leu Asn Ile Thr Phe Pro Thr Phe Pro Met Ala Thr Phe Asp Lys Lys Thr Lys Lys Lys Asn Asn Lys Lys His  Asn Lys Gly Val  Asp Asn Lys Val Ser Met Asn Lys Se
TATCCGTTTCACTTTACTTACAAGTATTCTCAACAACCTTACCAAAGAAAGTAACTTTACCAGATGTTTCAGTTACTTGAGGATCAGCAGCATTC
r Asp Thr Lys Lys Cys Thr Asn Glu Val Val Lys Gly Phe Phe Thr Val Lys Gly Ser Thr Glu Pro Ser Val Gln Pro Asp Ala Asn  T
```

TABLE 3-continued

```
GTTGCAAATGCAATAAAATTAAGCTACCAAGAAGTGTTTTTCATAATAAATTGCTCCAATAAAGAGGTTTGTGCCTTATAAATAAGGCAATAA
▼hr Ala Phe Ala Leu Ile Phe Gly Leu Thr Lys Lys Met Ile Phe Gln Glu Met

AGATTAATATAAACCGTTTATTTAAAATGCCAAAGGCTTAATAAACAGCAAACTTGTTTTCCAAAAAAGTAAAAACTCTTCCATTATATATA

TATATATATATAATTAAAAGCCCTTTTTGAAAAATTTCATATTTTTTGAATTAATTCGCTGTAGGTGGGTTTTTGCCCACATGGAGACATATA

AAAAGATTTGTAGGGTGGGCGTAAGCCACGCGGAAACATCATCAAACAATCTGTAATGTTGTATTAGGCACGGTGGGCTTATGCCTCGCTACGGG

GAAATGAATAAGGATAAATATGGGCTTAGCCCAGTTGATTTAATTATGTGAAATGGGGAAAACAATGTTTAAAAAACACTTTATTTT
▲Met Asn Lys Asp Lys Ile Gly Leu Ser Pro Val Tyr Gly Phe Asn Tyr Val Glu Met Gly Lys Thr Met Phe Lys Lys Thr Leu Leu Phe Ph
TACCGCACTATTTTTTGCCGGCATTTCAGCCAATGCACAGATGTTATCACTGGCACCAGAGTGATTTATCCGCTGGGCAAAAA
▲eThr Ala Leu Phe Phe Ala Ala Leu Cys Ala Phe Ser Ala Asn Ala Asp Val Ile Ile Thr Gly Thr Arg Val Ile Tyr Pro Ala Gly Gln Lys A
ATGTTATCGTGAAGTTAGAAAACATGATGAATTCGGCAGCATTGGTGCAAGCCTGGATTGATAATGCCAATCCAAATGCCGATCCAAAATAG CC
▲sn Val Ile Val Lys Leu Glu Asn Asn Asp Asp Ser Ala Ala Leu Val Gln Ala Trp Ile Asp Asn Ala Asn Pro Lys Tyr Thr

AAAACCCCTTTTGTGATTACCCCGCCTGTTGCTCGAGTGGAAGCGAAATCAGGGCAAAGTTTGCGGATTACGTTCACAGGCAGGCAGCCTTTACC
▲Lys Thr Pro Phe Val Ile Thr Pro Pro Val Ala Arg Val Glu Ala Lys Ser Gly Gln Ser Leu Arg Ile Thr Phe Thr Gly Ser Glu Pro Leu Pr
TGATGATCGCGAAAGCCTCTTTATTTATTTCAGTAATATTCCGCGAAACACGGCATTTCTGCAAAACACGGCAGCTTTATGCAAA
▲oAsp Asp Arg Glu Ser Leu Phe Tyr Phe Asn Leu Leu Asp Ile Pro Pro Lys Pro Asp Ala Ala Phe Leu Ala Lys His Gly Ser Phe Met Gln I
TTGGGCATTCGCTCACGTTTGAAGTTGTTTTATCGCCCTGCAAACTCTCGATGGATTCTGGTTGTTACATCAAATAAACCTGCAATGAAAAAGTAGTTTAAGCCACA
▲le  Ala  Ile Arg Ser Ala Arg Leu Lys Leu Phe Tyr Arg Pro Ala Lys Leu Ser Met Asp Ser Arg Asp Ala Met Lys Lys Ala Thr
CCTGAAGGGGGTGTTGGTGGATAATCAAACCCCTTATTATATGAACTACATTGGTTTGTTACATCAAATAAACCTGCGAAAAATGTCAAATGGT
▲Pro Glu Gly Val Leu Val Asp Asn Gln Thr Pro Tyr Tyr Met Asn Tyr Ile  Gly Leu Leu His Gln Asn Lys Pro Ala Lys Asn Val Lys Met Va
TGCCCCTTTTCTCAAGCGTATTTGAAGCCAAAGGCGTTCTCGGCGATAAATTGAAATGGATTGGTTAATGAATTACCGTGCCGACCAAG
▲l Ala Pro Phe Ser Gln His Ala Val Phe Glu Ala Lys Gly Val Arg Ser Gly Val Asp Lys Gly Lys Leu Val Leu Val Asn Asp Tyr Gly Ala Asp Gln G
AAGGCGAAGCCATGCTCAATAATAGCGAACTAGTGTAGGGTGGGCTTTAGACCACCGATTAACCATAACAAAGGTGGGCTGAAGCCCACCTAC
▲lu Gly Glu Ala Ile Ala Gln
AACCACAAAGAACGATTAATCGTGAAAACAAAAATTTTTCCCTTAAATAAATAAAATGCGTTTGCTTGTTCCGATTTAATGTAAAAAATGCCGTGTTACCA

GGGCGGAGATCAATTGATGCCTCTCTTTGGGGAGATGGTTCGGTGTTGGGCGTAAGGCGTAAGAAAAAGGCGTAAGCGATATATTTTGGGCGTTGATAATCCTGCCACAGGTCGACAGAATT

GGGCGTTATTACGCTAAACTTCAAGAAATCTATGTGAAGATTTGAAGGCGTAAGCCATTGTGAAATCGCCAATTCAGAAGATGACACTTGTGTCTTTGCTT

ATGCTTTACGCTGCTAAACTTCAAGAAAATGCTGATTTGATGAGATGAAGCCATTGTGAAATCGCCAATTCAGAAGATGACACTTGTGTCTTTGCTT
▲Met Leu Asp Leu Met Asp Ala Ile  Val Lys Ser Pro Asn Ser Glu Asp Asp Thr Cys Val Phe Ala S

CTGATGCTATTCCTAAAGGCACGTTTGAATATCAAAGGCGGGCGAAATGAAATTGAAACTTGAGCTCCCTCAAGCTCTCTACTATTCCGCCGACCAAGA
▲er Asp Ala Ile Pro Lys Gly Thr Phe Glu Tyr Gln Ser Gly Met Lys Glu Met Lys Lys Leu Glu Leu Pro Gln Ala Leu Thr Ile  Arg Arg Pro Arg
GGCTATATTGCGGCCTCTCGCTGGCAAACTGGCACCAAATTACGACATATCGTCTGGTAAATCCCGAAGTAAA
▲Gly Tyr Ile  Ala Pro Ser Arg Thr Gly Thr Gly Thr Asn Ala Ala Phe Ala Asn Tyr Asp Ile Asn Tyr Tyr Arg Ser Gly Asn Pro Glu Val Ly
ATCCGAAAGTTGTATGTGGCTTGCCGTAGTGGCGTAAATTTTGCAACTGGGCATAGCGGTCATAGCGGCAGTTTTAGCCGTTTGAAAACCAAA
▲s Ser Glu Ser Leu Tyr Val Gly Leu Arg Ser Gly Val Asn Phe Ala Leu Arg Arg His Ser Gly Ser Phe Ser Arg Phe Ser Glu Asn Gln S

GTAGCTCGGGTTTTACTGATAAGGGCAAAAATCATTACGAACGTGGCGATACCTATTTACAACGAGATTTCGCCCTGCTTCGTTGGCCAATGTCACT
▲er Ser Gly Phe Thr Asp Lys Gly Lys Asn His Tyr Glu Gly Asp Thr Tyr Leu Gln Arg Asp Phe Ala Leu Leu Arg Asn Val Thr
GTTGGGGATTTTTTCAGCACGTGCCCGCATTGGCGAAAATTTTTGTATGCGTGGTTGCGATTGCCTCTGATGATAGAATGCTTGCCCATACACA
▲Val Gly Asp Phe Ser Thr Ala Arg Ile  Gly Glu Asn Phe Gly Met Arg Gly Leu Arg Ile  Ala Ser Asp Asp Arg Met Leu Ala Pro Ser Gl
ACGTGGTTGTTTTTGCCCCAGTGGCGTGCCGTGGCAAACGCATGGCAATCAGCATCAAACAAAATGCTATACGATTTATCAAATCACCGTTC
▲nArg Thr Arg Pro Val Val Phe Ala Pro Ser Gln Val Ala Val Arg Gly Val Val Asn Thr Asn Ala Lys Asn Gly Tyr Thr Ile Tyr Val P
CCGCAGGGCCTTTCGTGGATAACGATTTGTATGCCAGCGGTTATAACGGTTATAACGCGGTTATGCCAGCGATTTAACGGTGAAATCCAAGAAAGTGATGATGATGTAAAGTGCGGTCA
▲ro Ala Gly Pro Phe Val Ile  Asn Asp Leu Tyr Ser Ala Ser Gly Tyr Ser Gly Leu Thr Val Glu Ile  Gln Glu Ser Gly Asp Gly Ser Val Arg Ser
TTTAATTGTGCCGTTTCTAATCTGCCCGTTAATGCGTGTGCGATTAAGTGCGTTAATCAATTAGCTGCGGACGTTATCGAATTGACGCGCAC
▲Phe Ile  Val Pro Phe Ser Asn Leu Ala Pro Leu Met Arg Val Gly His Arg Leu Tyr Gln Leu Ala Gly Arg Tyr Arg Ile  Asp Ser Arg Th
```

TABLE 3-continued

```
CTTTGATGAACGTGTTGTTGCAAGGCGTGTTGCAATATGGTTTAACTAATCATTCACGTGAATTCAAGCCTGCTTTATACACGTCATTATCGTG
r.Phe Asp Glu Arg Val Val Leu Gln Gly Val Leu Thr Asn His Leu Thr Leu Asn Ser Leu Tyr Thr Arg His Tyr Arg A
CAGGGCTGTTTTGGTTTTGGTTTTAAATACCGATTGGGCGTTTTCTGATGCCACTGGTCCACGCAGTTCCGCTAAAACATGGAGC
la Gly Leu Phe Gly Phe Gly Leu Asn Thr Pro Ile Gly Ala Phe Ser Ala Asp Thr Trp Ser His Ala Glu Phe Pro Leu Lys His Val Ser
AAAAACGGCTACAGTTGCACGGCAGTTATAGTATTAACTTCAATGAAAGTGGCACCAATATCAGTTGGCAGCCTATCGTTGCTATTCTCACGGGA
Lys Asn Gly Tyr Ser Leu His Gly Ser Tyr Ser Ile Asn Phe Asn Glu Ser Gly Thr Asn Ile Thr Leu Ala Ala Tyr Arg Tyr Ser Arg As
TTTTACACCTTAAGCGACACCATTGGTCTTAACCGCACTTTCAGACAATTTAGCGGTGCGTATTTGCCTGAAATTTACCGCCCAAAAAATCAGT
p.Phe Tyr Thr Leu Ser Asp Thr Ile Gly Leu Asn Arg Thr Phe Arg Gln Phe Ser Gly Ala Tyr Leu Pro Glu Ile Tyr Arg Pro Lys Asn Gln P
TTCAAGTGAGTTTAAGCCAAAGTTGGGAATTGGGAACTCTATCTTCAGGACAAACCTATAATTATTGGGAAAACGTTGGCACGAATACG
he Gln Val Ser Leu Ser Gln Ser Leu Gly Asn Trp Gly Thr Leu Ser Gly Gln Thr Tyr Asn Tyr Trp Glu Lys Arg Gly Thr Asn Thr
CAATATCAAGTTGCCTATTCAAACAGCTTCCACATTCTTAATTACTCTGTAAACCTCTCACAGAGTATTGATAAAGAAACCGGCAAACGTGACAA
Gln Tyr Gln Val Ala Tyr Ile Gln Thr Ala Ser Thr Ser Leu Ile Thr Leu Asn Pro Val Asn Leu Ser Gln Ser Ile Asp Lys Glu Thr Gly Lys Arg Asp As
CAGCAATTTATTAAGTCTCAGCCTGCCGATAACCATTCTGCAGATAGTATTCTCCAGTGGTAACGATATTAACCAACGACTTG
n Ser Ile Tyr Leu Ser Leu Pro Leu Gly Asn His Ser Ala Asp Ser Ser Tyr Ser Arg Asn Gly Asn Asp Ile Asn Gln Arg Leu G
GCCTAAATGGCTCTTTGGTGAACGTCATCAATGAGTTATGGTAATCAAGCCTCCAATAACAAGGCTATCGCAGTTATGACGGTAATCTT
ly Val Asn Gly Ser Phe Gly Arg His Gln Thr Ser Tyr Gly Ile Asn Ala Ser Arg Asn Gln Gly Tyr Arg Ser Tyr Asp Gly Asn Leu
TCGCATAACAATAGCATTGGTAGTTACCGTGCTCTTATTCACGTGATAGCTCCAAAAATCGCTCCATCTCACTGGGCGCAAGCGGTGCTGTCGT
Ser His Asn Asn Ser Ile Gly Ser Tyr Arg Ala Ser Tyr Ser Arg Asp Ser Arg Leu Lys Asn Ala Ser Ile Ser Leu Gly Ala Ser Gly Val Va
GGCGCACAAACACGTATTACCTTAAGCCAACCTGTTGCGAAAGTTTTGCCATTATTCACGCAGGACGCAAAAGTGAATCAG
l Ala His Gly Ile Thr Leu Ser Gln Pro Val Gly Ser Phe Ala Ile His Ala Lys Asp Ala Ala Gly Ala Lys Val Glu Ser G
GTGTCCAAATGTGAGCTTTGATTATTTCGGCAATGCGTATGCCTTACACCAGCCCGTATGAAAATCAATTATATCGGTATCAATCCATCTGATGCG
ly Ala Asn Val Ser Leu Asp Tyr Phe Gly Asn Ala Val Met Pro Tyr Phe Gly Gln Ile Asn Tyr Ile Gly Ile Glu Asn Pro Ser Asp Ala
GAGGCGAATGTGAATTTGAAGCCACTGAACGCCAAATCATTCCGTGCAAATCAATTAGCTTAGTAGATTTCCACGGCAAAATACAAT
Glu Ala Asn Val Glu Phe Glu Ala Thr Thr Thr Ser Tyr Ile Gly Ile Glu Pro Arg Asn Ser Ile Ser Leu Val Asp Phe Arg Gly Lys Asn Thr Me
GGTGTTATTTAACCTCACTTTGCCAAATGGCGAGCCAGTTGCCATCCAATGGCATCGACAGCCAGTGCAAGTAGGCAAGGGCATTTGTGGGCGATGTGTGC
t Val Leu Phe Asn Leu Thr Leu Pro Asn Gly Glu Pro Val Pro Met Ala Ser Thr Ala Gln Asn Ser Gln Gly Ala Phe Val Gly Val Val G
AAGGTGGTGTCTTTTCGTCTAATAAACTTACCCAGCCAAAAGGCGAGTTAATCGTCAAATGGGGTGAGCGAGAAAGCGAACAATGCCGTTTCCAA
ly Gly Val Val Phe Ser Ser Asn Lys Leu Thr Gln Pro Lys Gly Glu Leu Ile Val Lys Trp Gly Glu Arg Glu Ser Arg Cys Phe Gln
TATCAAGTTGATTTGGATAACGCACAAAACACAAAGTCACGATATTCAATGCAAATCGCAAAATAATAATTGAAGAGATTTATGCAAAAACA
Tyr Gln Val Asp Leu Asp Asn Ala Gln Asn Thr Gln Ser His Asp Ile Gln Cys Lys Thr Ala Lys ▲Met Gln Thr
CCCAAAAATTAACCGCCCTTTCATCAAAATCCTGCTACTGTAGTGGAGCAAATATAGTGGAGCAAATTATAGTGGCTCAAAATGCTT
Pro Lys Leu Phe His Gln Ile Ser Leu Thr Ala Thr Thr Cys Ser Ser Gly Ala Asn Tyr Ser Gly Lys Ser Cys Ph
TAGGTTTCATCGTCTGGCCTGCTGCTGCGTGCTTGCTGATTGCATTGTGGCACTGCCTGCTTATGCTTACGATGGCAGAGTGACCTTTC
e Arg Phe His Arg Leu Ala Leu Leu Ala Cys Val Leu Leu Asp Cys Ile Val Ala Leu Pro Ala Tyr Ala Tyr Asp Val Arg Val Thr Phe G
AAGGGGAGATTTTAAGTGATGGCACTTGTAAAATTGAAACAGACAGCCAAAATCGCACGGTTACCCTGCCAACAGTGGAAAAGCTAATTTAAGC
ln Gly Glu Ile Leu Ser Asp Gly Thr Cys Lys Ile Glu Thr Asp Ser Gln Asn Arg Thr Val Pro Thr Val Gly Lys Ala Asn Leu Ser
CACGCAGGGCAAACCGCCGCCGTGCTTTTCATCAATGTCTTAAAGATGCAATGCAATGCAGATTCTATGAAAGCTATCTGGCTTTAAAGC
His Ala Gly Gln Thr Ala Ala Pro Val Pro Phe Ser Ile Thr Leu Leu Glu Cys Asn Ala Gly Asp Ala Met Lys Ala Asn Leu Ala Phe Lys Gl
GGGAGACAACAACACGGCAATCTTATCTTCCAATAAGGCAGGCAACGGCAAACGCCACCAACGTGGGCATTCAAATTGTCAAAGCCGATGGCA
y Gly Asp Asn Asn Thr Arg Gln Ser Tyr Leu Ser Ser Asn Lys Ala Gly Asn Gly Lys Ala Thr Ala Asn Val Gly Ile Gln Ile Val Lys Ala Asp Gly I
TAGGCACGCCTATCAAGGTGGACGGCACCGAAGTGAAGCCCGACAAGCCCGACAAGGTAAAGCCACAGTTATTCAACCCCGT
le Gly Thr Pro Ile Lys Val Asp Gly Thr Glu Ala Asn Ser Glu Lys Ala Pro Asp Thr Gly Lys Ala Gln Asn Gly Thr Val Ile Gln Pro Arg
TTTGGCTACTTTGGCTCGTTATTACGCCACAGGTGAAGCCACCGACGTTGAAGCCGACGTTGACCACTGCAACTTTTGAAGTGCAGTATAACTAAATA
Phe Gly Tyr Phe Gly Ser Leu Leu Arg His Arg
TTTATTATCCAGTGAAAAAATGAATAAGAAATCGTATATAAATCATTACTTAACTTATTTTAAAGTTACTACTTTACTCTTCAAGTA
ATCCTGTATGGCAAATATAAAACAGTTCAGGGAACACTAGTGTTTTTCCACTTCTAACAAGAACTTTCACATTTAATGGCAATTGCAATGG
▲Met Asn Lys Lys Ser Tyr Ile Asn His Tyr Leu Phe Asn His Tyr Leu Phe Thr Leu Leu Phe Thr Leu Ser Ala
AATGTGAGTGCTCTACAAACCAGCTCTATATTGTTTCCTCTCAAGCAAGATAATCAGCAGTAGCAAGCTTAGCTTGTACAGTTAATC
sn Pro Val Trp Ala Asn Ile Lys Thr Val Gln Gly Thr Thr Ser Gly Phe Pro Leu Leu Thr Arg Phe Pro Thr Phe Asn Gly Val Ser Leu Trp
AACAAATTCATTAGCTCCATTTAATAATGATTAATACGAAATCAGCAGTAGAGCTAGGTTGTATAGCTTGTGCCGATTATGTACTAGTAATC
Asn Val Ser Ala Leu Gln Pro Ala Tyr Ile Val Ser Arg Asn Ala Gly Asp Ala Asn Leu Asp Thr Val His Ile Gln Ser Ala Pr
ACAAATTCATTAGCTCCATTAATAATAGGATTAATACGAAATCAGCAGGATATAGCTAGCTTGTACAGTTAATC
o Thr Asn Ser Leu Ala Pro Phe Asn Asn Trp Ile Asn Thr Arg Lys Ser Ala Val Glu Val Gly Leu Gly Tyr Ser Phe Ala Gly Ile Thr Cys Thr Ser Asn P
```

TABLE 3-continued

```
CTTGCCCAACAATGAAATTACCATTATTATTCATCCTGATCTTACTAATTTAACTCCACCTGGAAAGAAAAATTCTGATGGAGGGAGATTTTT
▲ro Cys Pro Thr Met Lys Leu Pro Leu Phe His Pro Asp Leu Thr Asn Leu Thr Pro Pro Gly Lys Lys Asn Ser Asp Gly Gly Glu Ile Phe
AAATTACATAAATGAATCTAATTTAGGGGTCTCTTTCAAATTGGAGTAAAAACGAATACTTCTCTAGAATTGGGTTAATGCTAAGAATAATTTAG
▲Lys Leu His Asn Glu Ser Asn Leu Gly Val Ser Phe Gln Ile Gly Val Lys Thr Asn Thr Ser Leu Asp Trp Val Asn Ala Lys Asn Phe Se
CTCTCTAAAAGTTTTAATGGTGCCTTTTAATTCTAGCGATAAAATATCTTTGCATTTACGTGCTAAATTCATTTATTAACAGATTTTCATCGC
▲r Ser Leu Lys Val Leu Met Val Pro Phe Asn Ser Ser Asp Lys Ile Ser Leu His Leu Arg Ala Lys Phe His Leu Phe Ile Asp Phe Ser Ser L
TAAATAATGATATTACTATTGACCCTATGAATACTAGTATAGGCAAAATTAATCTTGAAACGTGGCGTGCTCAACAGGCAATTTTCTGTTAAA
▲eu Asn Asn Asp Ile  Thr Ile  Asp Pro Met Asn Thr Ser Ile  Gly Lys Ile  Asn Leu Glu Thr Trp Arg Gly Val Ser Gly Asn Phe Ser Val Lys
TATGTAGGTGAGGATAAGGAGAATATATCTATTTTCTTTAATACACCTAAAAATTATTCTAAAAAACAACAACGCCGATGTACTCTGAATAATGC
▲Tyr Val Gly Glu Asp Lys Gly Asp Ile  Ser Ile  Phe Phe Asn Thr Pro Lys Ile  Ile Leu Lys Lys Gln Arg Arg Cys Thr Leu Asn Asn Al
TCCAGTGAGCCCAAATCCAGTTAAATTACGAGCGTAAAAAACGTGAATTGGAGGCACAAAGTGAATGAAGGTGGACATTTCAGTTAAGAG
▲aPro Val Ser Pro Asn Pro Val Lys Leu Arg Ala Val Lys Lys Gln Arg Arg Thr Glu Leu Gln Arg Glu Glu Gly Thr Val Lys Lys Glu Arg Val
TAAATTGTGACAATACCCACTATAATAAAGCCAACGGCAAATGGTTATTTCCGTAGTGAAAGTTACTTTTACGACGAAGATGTACAACGAAT
▲aPro Val Ser Pro Asn Pro Val Lys Leu Arg Ala Val Lys Glu Gln Ala Gln Ser Glu Met Glu Gly Gly Thr Phe Gln Leu Arg V
AATGGAACAAATGACTTACTTCGCACCCAAACAGGCAGCGGACAAGCCACAGCCGTTAGCTTAAGAATCAAACGAGAAAAATGGTACAGAAACCGT
▲al Asn Cys Asp Asn Thr Thr Tyr Asn Lys Ala Asn Gly Lys Trp Leu Phe Pro Val Val Lys Val Thr Phe Thr Asp Gln Asp Gly Thr Thr Asn
AATGGAACAAATGACTTACTTCGCACCCAAACAGGCAGCGGACAAGCCACAGCCGTTAGCTTAAGAATCAAACGAGAAAAATGGTACAGAAACCGT
▲Asn Gly Thr Asn Asp Leu Leu Arg Thr Gln Thr Gly Ser Gly Ala Thr Gly Val Ser Leu Arg Ile  Lys Arg Glu Asn Gly Thr Glu Thr Va
AAAATACGGTGCTGATTCTGCTCAAATGGGAATTGCTGGACAATTTGAATTACGAAAACAATCCCTGCTGGTGGAGATCAAATATGCTGAAG
▲Asn Gly Thr Asn Asp Leu Leu Arg Thr Gln Thr Gly Ser Gly Ala Thr Gly Val Ser Leu Arg Ile Lys Arg Glu Asn Gly Thr Glu Thr Va
AAACTTTCAAAGTCTATTACGTAAAAGACTCAACAAGAGGCACCTTAATCGAAGGAAAAGTCAAAGCCCGCCCACTTTCACAATGTCATATCAA
▲l Lys Tyr Gly Ala Asp Ser Ala Gln Met Gly Asn Ala Gly Gln Phe Glu Leu Arg Lys Gln Pro Ser Pro Ala Gly Gly Asp Gly Gln Tyr Ala Glu G
lu Thr Phe Lys Val Tyr Tyr Val Lys Asp Ser Thr Arg Gly Thr Leu Ile  Glu Gly Lys Val Lys Ala Ala Ala Thr Phe Thr Met Ser Tyr Gln

TAATAATGTCGGTGGGAATATAAAGGCTGAAGGTTTAAACTTCAGTCTTTTTTATAGGAAAAATACCATTGCAACTTTAAGGATAAAATTTAT
CCTAAGCACACAATTTTTATAAGAATAGGTCAAATTATGTTAGCTCAAAGCAAAATATAGAAAAAGATTACAAACAACCAGATTTTACGGTCACAGACA
▲                                                     ▲Met Leu Ala Lys Ala Lys Tyr Arg Lys Tyr Val Lys Gln Pro Asp Phe Thr Val Thr Asp I
TTTTATTTAGATTTTCAACTTGATCCTAAAAAAACTGTCGTGACTGCAACCACAAATTCCAACGCTTAAATAATGAAGCGACGTCTTTACGTTTA
▲le Tyr Leu Asp Phe Gln Leu Asp Pro Lys Asn Thr Val Val Thr Ala Thr Thr Lys Phe Gln Arg Leu Asn Asn Glu Ala Thr Ser Leu Arg Leu
GACGGGCATAGCTTCCAGTTTTCTCTATTAAATTAATGCGAGCCATTTCTGATTATCAACAAGATGCGAGAGTTTAACGCTCGATTTAAA
▲Asp Gly His Ser Phe Phe Gln Phe Ser Ser Ile  Lys Phe Asn Gly Pro Phe Ser Asp Tyr Gln Glu Asp Gly Ser Leu Thr Leu Asp Leu Ly
AGACAAAAGTGCCGGATGAATTGAGCTTGAAATTGAAATGTGACCTGAAATACGTCCATTACAAGGGCTATATCAGTCTGGCCAAG
▲s Asp Lys Ser Ala Asp Gly Pro Phe Glu Ile  Val Thr Phe Leu Val Pro Ala Glu Asn Thr Ser Leu Gln Gly Leu Tyr Gln Ser Gly Glu G
GTATTGTACGCAATCTGAGGCGGAAGGTTTCCGTCAAATCACTTATATGCTTGATCGTCGTCGATGTGCCGCGTTATATAATCAAATTACG
▲ly Ile  Cys Thr Gln Cys Glu Ala Glu Gly Phe Arg Gln Ile  Thr Tyr Met Leu Asp Arg Pro Asp Val Leu Ala Arg Tyr Ile  Ile  Lys Thr
GCAGATATAAAAACCAAATATCCATTCTTACTGTGCAATGGTAATCGCATTCGAATTGCAAGTTGGCAATTAGAAGATGTCGCAATTGGGTGAAGTGAATGA
▲Ala Asp Ile Lys Thr Gln Tyr Pro Phe Leu Leu Ser Asn Gly Asn Arg Ile  Ala Ser Gly Glu Leu Glu Asp Gly Leu Glu His Trp Val Glu Trp Asn As
TCCTTCCCAAAACCAAGCTATTTATTTGCTTTAGTGCGGAGATTNNGGTTTATTACAAGATAANTTTATTACTAAAAGTGGTCGTGAAGTGG
▲pPro Phe Pro Ser Tyr Leu Phe Ala Leu Val Ala Gly Asp Leu Leu Asp Asp ??? Phe Ile  Thr Lys Ser Gly Arg Glu Val A
CTTTAGAGCTTTATGTGGATCGCGGTAATCTTAACCGTGCAACTGGGCAATGGAAAGTCTGAAAAAAGCGATGAAATGGGATGAAGATCGCTTT
▲la Leu Glu Leu Tyr Val Asp Arg Gly Asn Leu Asn Arg Ala Thr Gly Ala Met Glu Ser Leu Lys Lys Ala Met Lys Trp Asp Glu Asp Arg Phe

AATTTAGAATTTTACCTAGATATTTATATGATCGCGCCGCCGATTCCTCCAATATGGAAGCAATGGAAAATAAAGGATTAAATATCTTTAACTC
▲Ile  Leu Glu Phe Tyr Leu Asp Ile  Tyr Met Ile  Ala Ala Ala Asp Ser Asn Met Gly Ala Met Glu Asn Lys Gly Leu Asn Ile  Phe Asn Se
TAAATTGGTGTTGGCAAATCCAAACGCAACAGATGAAGATTATCTTTGCACGAATGAAAGTGTCATTGATTGCACGAATATTCCATAACTGACGG
▲r Lys Leu Val Leu Ala Asn Pro Gln Thr Ala Thr Asp Glu Asp Tyr Leu Val Ile  Glu Ser Val Ile  Ala His Gly Tyr Ser His Asn Trp Thr G

GAAACCGTGTAACCCGCCGAGAATGGGTTCAACTAGGTTTGAAGAAGGTTAACGGCTTCCGGAACAACATTTCTCAGATCAGTTCTCCGGCCGG
▲ly Asn Arg Val Thr Arg Arg Asp Arg Phe Asn
AACCGATTAATTAAGGGAAAATTTTCCG
```

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 9432 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: complement (1882..2532)

( i x ) FEATURE:
        ( A ) NAME/KEY: CDS
        ( B ) LOCATION: 2854..3630

( i x ) FEATURE:
        ( A ) NAME/KEY: CDS
        ( B ) LOCATION: 4016..6238

( i x ) FEATURE:
        ( A ) NAME/KEY: CDS
        ( B ) LOCATION: 6259..6873

( i x ) FEATURE:
        ( A ) NAME/KEY: CDS
        ( B ) LOCATION: 6955..8265

( i x ) FEATURE:
        ( A ) NAME/KEY: CDS
        ( B ) LOCATION: 8395..9340

( x i ) SEQUENCE DESCRIPTION: SEQ ID NO:1:

```
AAGCTTGCAT GCCTGCAGGT CGACTCTAGA GGATCATTCC ATTGTGTTTT ATCTTTTAAT      60
AAACACCAAG GTGAGGTAGA AATATTCAGT TCATCAAGCA AGGATTTTTG CGTAAAACGA     120
TCGGCTAATA ATCCAAATAC ATGTTGATTA ACGAAGTTTT TATGATTGCT GAGTAATTCA     180
GTCAAAGGCG TTTTTTCCCA GCGTTCAATT TCCGCCGTGA TGATCGCATT TTCAGGTAAG     240
TCAAAAACTG GCGCATTGAA GGCTAAGGGT TCAACATAAA TATCTAAAGG TGCACCAGCG     300
TAACCTAACA TTCTGCCGAG TTGTCCGTTG CCGAGAACAT AAACGGTTGG GTATAAGGTG     360
GAGTTTTGCA TAATATTTCT CGTTAAATTT ACGAAAAAAC AACCGCACTT TAAAAGTGCG     420
GTCAGATCTG AAGATATTTT TATGTGCGTG GATCGGGATT GTCCAGTACA GCACGAGTTT     480
GGCTTTCACG GAAAGATTGC AAGCGTGAAA GCAATTCTGC ATCCCAACCT GCTAGAATTT     540
GGGCTGCTAA CAACCCAGCA TTTGCCGCGC CTGCAGAGCC AATCGCTAAT GTTCGACTG      600
GAATCCCTTT TGGCATTTGC ACAATTGAAT AAAGGCTATC CACACCACTT AACATAGAAC     660
TTTTTACTGG CACCCCCAGC ACTGGCACAA GTGTTTTGGC TGCGATCATA CCAGGTAAAT     720
GTGCCGCACC GCCTGCACCA GCAATAATTA CTTTATAGCC ATTTTTTTGT GCATTTTCGG     780
CAAATTCGAA AAGTTTATCA GGCGTACGAT GGGCAGAGAC GACTTCCACA TGATAAGGCA     840
CGTTTAATTC ATCTAAAATC TGAGTTGCCT CTTGCATAGT AGCCCAATCA CTTTTTGACC     900
CCATCACAAC GGCAATTTGT GCAGTTTTTG ACATGCTATT TTCTCAATTT TCTAATTAAA     960
AACGTGGTGT AGAATAGCAT AGATTACATA TATCGAGCAA ACGTTGCTA TTTATGTACG    1020
TATTAATGGG GATTATTTTA TAATTATTTG ATTTTTAAAT TTTAGTAACT ATACTTGATA    1080
```

-continued

| | | | | | |
|---|---|---|---|---|---|
| CCAAATTAAT | GGGCGATAGT | TTATATGGGA | CGAACTGAAA | AATTATTAGA | TAAGCTCGCA | 1140 |
| CAATCAAAAT | CTACATTTAA | TTGGAATGAA | TTAGTTTCTT | TGTTAGCTCA | ACAAGGTTAT | 1200 |
| GAAAAGCGAG | AAATGGCAGG | TTCTCGAGTG | AGATTTATA | ATAGAACACT | CGAACATATG | 1260 |
| ATTTTGTTAC | ACAAGCCTCA | TCCTGAAAAT | TATATTAAAG | GCGGTGTTTT | AAAGTCAGTG | 1320 |
| AAAGAATCAT | TAAAACAGGT | AGGTATTCTA | TGAAGTTATT | AAATTATAAA | GGTTATGTTG | 1380 |
| GCACGATTGA | GGCGGATTTA | GAAAACAATA | TATTATTTGG | CAAACTTGCT | TACATTCGTG | 1440 |
| ATTTAGTGAC | TTACGAAGCA | GAGTCATTAT | CTGAGTTAGA | AAAAGAATTT | CATCAATCTG | 1500 |
| TTGATTTATA | TTTACAAGAT | TGTTTGGAAT | TAGGTAAAGA | ACCGAATAAG | CCTTTTAAAG | 1560 |
| GTGTATTTAA | TGTACGAATT | GGCGAGGAAT | TGCATAGAGA | AGCAACGATC | ATAGCTGGCG | 1620 |
| ATCGTTCTCT | TAATGCTTTT | GTGACGGAAG | CAATTAAAGA | AAAAATTTTT | CGTGAAAAAC | 1680 |
| CAAGTTAAG | ATAACAAAAC | GTATTTACAT | TTTTTTTCAT | CACGTAGGCT | GGGCGTAAGC | 1740 |
| CCATGTAGAG | ACACATAAAA | AAGATTTGTA | GGCTAGGCGT | AAGCTCACGT | GGATACATAT | 1800 |
| AAAAAGATT | TGTAGGGTGG | GCGTAAGCCC | ACGCAGGATA | TAACAAACAC | GTGGGCTTAG | 1860 |
| ATTGCATTAC | ATTAGGAATT | ATTCGTAAGC | AATTTGGAAA | TCAACTGAGG | ATTCTACTTT | 1920 |
| ACCAGCTTCC | GCTTGAGCTG | TTGCATAGTA | TCTAGCGATA | TAGTGTAATT | TCACATTGTT | 1980 |
| TTCACCGTTA | ATTGTAGCTT | TTCCTGAAAT | ATGATTTTA | TTCACAGTTT | GTTGTGTTGC | 2040 |
| AACGTCATTT | GTATTGCTAT | GCGTAAAATC | TGTTGTTCCG | TTGCCGACAA | CTTCAATTGC | 2100 |
| ATCTGTACCA | TTAGCATCAA | AAAGCTGGAT | ATTAACATTC | TGTGCAGCAT | CATTTCCTGA | 2160 |
| TTTTGTATTT | TTAATGTAT | ATTCATTATT | TTCATCTGCA | TTTTTCCAAG | AATAGAAATA | 2220 |
| AGCTCCAACT | TTTGTTGCAA | CAGGCTTATT | ATTAGTAGTA | GTAGTAGTAG | AACAATTTTC | 2280 |
| TAAATTAATT | GTAAATGGTG | TTGGCATCGC | TGTATCTTTT | TTAGTTTTA | AATGATTTTT | 2340 |
| ACCCACATCA | TTTAATACTA | CGCTCATATT | TTTACTATCC | GTTTCACTT | TACAAGTATT | 2400 |
| CTCAACAACC | TTACCAAAGA | AAGTAACTTT | ACCAGATGTT | TCAGTACTTA | CTTGAGGATC | 2460 |
| AGCAGCATTC | GTTGCAAATG | CCAATAAAAT | TAAGCTACCA | AGAAGTGTTT | TTTTCATAAT | 2520 |
| AAATTGCTCC | ATAAAGAGGT | TTGTGCCTTA | TAAATAAGGC | AATAAAGATT | AATATAAACC | 2580 |
| GTTATTAAA | ATGCCAAAGG | CTTAATAAAC | AGCAAACTTT | GTTTCCCAA | AAAAAGTAAA | 2640 |
| AAACTCTTCC | ATTATATATA | TATATATATA | TAATTAAAGC | CCTTTTTGAA | AAATTTCATA | 2700 |
| TTTTTTTGAA | TTAATTCGCT | GTAGGTTGGG | TTTTTGCCCA | CATGGAGACA | TATAAAAAAG | 2760 |
| ATTTGTAGGG | TGGGCGTAAG | CCCACGCGGA | ACATCATCAA | ACAACTGTAA | TGTTGTATTA | 2820 |
| GGCACGGTGG | GCTTATGCCT | CGCCTACGGG | GAA ATG AAT AAG GAT AAA TAT GGG | 2874 |
| | | | Met Asn Lys Asp Lys Tyr Gly | |
| | | | 1                5            | |

| CTT | AGC | CCA | GTT | TAT | GGA | TTT | AAT | TAT | GTT | GAA | ATG | GGG | AAA | ACA | ATG | 2922 |
|---|---|---|---|---|---|---|---|---|---|---|---|---|---|---|---|---|
| Leu | Ser | Pro | Val | Tyr | Gly | Phe | Asn | Tyr | Val | Glu | Met | Gly | Lys | Thr | Met | |
| | | 10 | | | | 15 | | | | | 20 | | | | | |

| TTT | AAA | AAA | ACA | CTT | TTA | TTT | TTT | ACC | GCA | CTA | TTT | TTT | GCC | GCA | CTT | 2970 |
|---|---|---|---|---|---|---|---|---|---|---|---|---|---|---|---|---|
| Phe | Lys | Lys | Thr | Leu | Leu | Phe | Phe | Thr | Ala | Leu | Phe | Phe | Ala | Ala | Leu | |
| | 25 | | | | | 30 | | | | | 35 | | | | | |

| TGT | GCA | TTT | TCA | GCC | AAT | GCA | GAT | GTG | ATT | ATC | ACT | GGC | ACC | AGA | GTG | 3018 |
|---|---|---|---|---|---|---|---|---|---|---|---|---|---|---|---|---|
| Cys | Ala | Phe | Ser | Ala | Asn | Ala | Asp | Val | Ile | Ile | Thr | Gly | Thr | Arg | Val | |
| 40 | | | | | 45 | | | | | 50 | | | | | 55 | |

| ATT | TAT | CCC | GCT | GGG | CAA | AAA | AAT | GTT | ATC | GTG | AAG | TTA | GAA | AAC | AAT | 3066 |
|---|---|---|---|---|---|---|---|---|---|---|---|---|---|---|---|---|
| Ile | Tyr | Pro | Ala | Gly | Gln | Lys | Asn | Val | Ile | Val | Lys | Leu | Glu | Asn | Asn | |
| | | | | 60 | | | | | 65 | | | | | 70 | | |

| GAT | GAT | TCG | GCA | GCA | TTG | GTG | CAA | GCC | TGG | ATT | GAT | AAT | GGC | AAT | CCA | 3114 |
|---|---|---|---|---|---|---|---|---|---|---|---|---|---|---|---|---|
| Asp | Asp | Ser | Ala | Ala | Leu | Val | Gln | Ala | Trp | Ile | Asp | Asn | Gly | Asn | Pro | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 75  |     |     |     |     | 80  |     |     |     |     |     | 85  |      |
| AAT | GCC | GAT | CCA | AAA | TAC | ACC | AAA | ACC | CCT | TTT | GTG | ATT | ACC | CCG | CCT | 3162 |
| Asn | Ala | Asp | Pro | Lys | Tyr | Thr | Lys | Thr | Pro | Phe | Val | Ile | Thr | Pro | Pro |      |
|     |     |     | 90  |     |     |     | 95  |     |     |     |     | 100 |     |     |     |      |
| GTT | GCT | CGA | GTG | GAA | GCG | AAA | TCA | GGG | CAA | AGT | TTG | CGG | ATT | ACG | TTC | 3210 |
| Val | Ala | Arg | Val | Glu | Ala | Lys | Ser | Gly | Gln | Ser | Leu | Arg | Ile | Thr | Phe |      |
|     | 105 |     |     |     | 110 |     |     |     |     | 115 |     |     |     |     |     |      |
| ACA | GGC | AGC | GAG | CCT | TTA | CCT | GAT | GAT | CGC | GAA | AGC | CTC | TTT | TAT | TTT | 3258 |
| Thr | Gly | Ser | Glu | Pro | Leu | Pro | Asp | Asp | Arg | Glu | Ser | Leu | Phe | Tyr | Phe |      |
| 120 |     |     |     |     | 125 |     |     |     | 130 |     |     |     |     |     | 135 |      |
| AAT | TTG | TTA | GAT | ATT | CCG | CCG | AAA | CCT | GAT | GCG | GCA | TTT | CTG | GCA | AAA | 3306 |
| Asn | Leu | Leu | Asp | Ile | Pro | Pro | Lys | Pro | Asp | Ala | Ala | Phe | Leu | Ala | Lys |      |
|     |     |     |     | 140 |     |     |     |     | 145 |     |     |     |     | 150 |     |      |
| CAC | GGC | AGC | TTT | ATG | CAA | ATT | GCC | ATT | CGC | TCA | CGT | TTG | AAG | TTG | TTT | 3354 |
| His | Gly | Ser | Phe | Met | Gln | Ile | Ala | Ile | Arg | Ser | Arg | Leu | Lys | Leu | Phe |      |
|     |     |     | 155 |     |     |     |     | 160 |     |     |     |     | 165 |     |     |      |
| TAT | CGC | CCT | GCG | AAA | CTC | TCG | ATG | GAT | TCT | CGT | GAT | GCA | ATG | AAA | AAA | 3402 |
| Tyr | Arg | Pro | Ala | Lys | Leu | Ser | Met | Asp | Ser | Arg | Asp | Ala | Met | Lys | Lys |      |
|     |     | 170 |     |     |     |     | 175 |     |     |     |     | 180 |     |     |     |      |
| GTA | GTG | TTT | AAA | GCC | ACA | CCT | GAA | GGG | GTG | TTG | GTG | GAT | AAT | CAA | ACC | 3450 |
| Val | Val | Phe | Lys | Ala | Thr | Pro | Glu | Gly | Val | Leu | Val | Asp | Asn | Gln | Thr |      |
|     | 185 |     |     |     |     | 190 |     |     |     |     | 195 |     |     |     |     |      |
| CCT | TAT | TAT | ATG | AAC | TAC | ATT | GGT | TTG | TTA | CAT | CAA | AAT | AAA | CCT | GCG | 3498 |
| Pro | Tyr | Tyr | Met | Asn | Tyr | Ile | Gly | Leu | Leu | His | Gln | Asn | Lys | Pro | Ala |      |
| 200 |     |     |     |     | 205 |     |     |     |     | 210 |     |     |     |     | 215 |      |
| AAA | AAT | GTC | AAA | ATG | GTT | GCC | CCT | TTT | TCT | CAA | GCG | GTA | TTT | GAA | GCC | 3546 |
| Lys | Asn | Val | Lys | Met | Val | Ala | Pro | Phe | Ser | Gln | Ala | Val | Phe | Glu | Ala |      |
|     |     |     |     | 220 |     |     |     |     | 225 |     |     |     |     | 230 |     |      |
| AAA | GGC | GTG | CGT | TCT | GGC | GAT | AAA | TTG | AAA | TGG | GTA | TTG | GTT | AAT | GAT | 3594 |
| Lys | Gly | Val | Arg | Ser | Gly | Asp | Lys | Leu | Lys | Trp | Val | Leu | Val | Asn | Asp |      |
|     |     |     | 235 |     |     |     |     | 240 |     |     |     |     | 245 |     |     |      |
| TAC | GGT | GCC | GAC | CAA | GAA | GGC | GAA | GCC | ATC | GCT | CAA | TAATAGCGAA |     |     |     | 3640 |
| Tyr | Gly | Ala | Asp | Gln | Glu | Gly | Glu | Ala | Ile | Ala | Gln |     |     |     |     |      |
|     |     | 250 |     |     |     |     | 255 |     |     |     |     |     |     |     |     |      |

| | | | | |
|---|---|---|---|---|
| CTAGTGTAGG | GTGGGCTTTA | GACCACCGAT | TAACCATAAC | AAAGGTGGGC | TGAAGCCCAC | 3700 |
| CCTACAACCA | CAAAGAACGA | TTAATCTGTG | AAAACAAAAA | TTTTTCCCTT | AAATAAAATT | 3760 |
| GCGTTTGCTT | GTTCACTGCT | ATTGGCAAAT | CCTTTAGCGT | GGGCGGGAGA | TCAATTTGAT | 3820 |
| GCCTCTCTTT | GGGGAGATGG | TTCGGTGTTG | GGCGTTGATT | TTGCCCGATT | TAATGTAAAA | 3880 |
| AATGCCGTGT | TACCAGGGCG | TTATGAAGCT | CAAATCTATG | TGAAATTTGA | AGAAAAGGC | 3940 |
| GTAAGCGATA | TTATTTTTGC | TGATAATCCT | GCCACAGGTC | GGACAGAATT | ATGCTTTACG | 4000 |
| CCTAAACTTC | AAGAA | ATG CTG GAT TTG ATG GAT GAA GCC ATT GTG AAA TCG | | | | 4051 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | Met | Leu | Asp | Leu | Met | Asp | Glu | Ala | Ile | Val | Lys | Ser |
|     |     |     |     |     |     | 1   |     |     |     | 5   |     |     |     |     | 10  |     |
| CCC | AAT | TCA | GAA | GAT | GAC | ACT | TGT | GTC | TTT | GCT | TCT | GAT | GCT | ATT | CCT | 4099 |
| Pro | Asn | Ser | Glu | Asp | Asp | Thr | Cys | Val | Phe | Ala | Ser | Asp | Ala | Ile | Pro |      |
|     |     | 15  |     |     |     |     | 20  |     |     |     |     | 25  |     |     |     |      |
| AAA | GGC | ACG | TTT | GAA | TAT | CAA | AGC | GGC | GAA | ATG | AAA | TTG | AAA | CTT | GAG | 4147 |
| Lys | Gly | Thr | Phe | Glu | Tyr | Gln | Ser | Gly | Glu | Met | Lys | Leu | Lys | Leu | Glu |      |
|     | 30  |     |     |     |     | 35  |     |     |     |     | 40  |     |     |     |     |      |
| CTC | CCT | CAA | GCT | CTC | ACT | ATT | CGC | CGA | CCA | AGA | GGC | TAT | ATT | GCG | CCA | 4195 |
| Leu | Pro | Gln | Ala | Leu | Thr | Ile | Arg | Arg | Pro | Arg | Gly | Tyr | Ile | Ala | Pro |      |
| 45  |     |     |     |     | 50  |     |     |     |     | 55  |     |     |     |     | 60  |      |
| TCT | CGC | TGG | CAA | ACT | GGC | ACC | AAT | GCC | GCT | TTT | GCA | AAT | TAC | GAT | ATC | 4243 |
| Ser | Arg | Trp | Gln | Thr | Gly | Thr | Asn | Ala | Ala | Phe | Ala | Asn | Tyr | Asp | Ile |      |
|     |     |     |     | 65  |     |     |     |     | 70  |     |     |     |     | 75  |     |      |
| AAC | TAT | TAT | CGT | TCT | GGT | AAT | CCC | GAA | GTA | AAA | TCC | GAA | AGT | TTG | TAT | 4291 |
| Asn | Tyr | Tyr | Arg | Ser | Gly | Asn | Pro | Glu | Val | Lys | Ser | Glu | Ser | Leu | Tyr |      |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |  80 |     |     |     |     | 85  |     |     |     |     | 90  |     |      |
| GTG | GGC | TTG | CGT | AGT | GGC | GTA | AAT | TTT | GGC | AAC | TGG | GCA | TTG | CGT | CAT | 4339 |
| Val | Gly | Leu | Arg | Ser | Gly | Val | Asn | Phe | Gly | Asn | Trp | Ala | Leu | Arg | His |      |
|     |     | 95  |     |     |     |     |     | 100 |     |     |     |     | 105 |     |     |      |
| AGC | GGC | AGT | TTT | AGC | CGT | TTT | GAA | AAC | CAA | AGT | AGC | TCG | GGT | TTT | ACT | 4387 |
| Ser | Gly | Ser | Phe | Ser | Arg | Phe | Glu | Asn | Gln | Ser | Ser | Ser | Gly | Phe | Thr |      |
|     | 110 |     |     |     |     |     | 115 |     |     |     |     | 120 |     |     |     |      |
| GAT | AAG | GGC | AAA | AAT | CAT | TAC | GAA | CGT | GGC | GAT | ACC | TAT | TTA | CAA | CGA | 4435 |
| Asp | Lys | Gly | Lys | Asn | His | Tyr | Glu | Arg | Gly | Asp | Thr | Tyr | Leu | Gln | Arg |      |
| 125 |     |     |     | 130 |     |     |     |     | 135 |     |     |     |     | 140 |     |      |
| GAT | TTC | GCC | CTG | CTT | CGT | GGC | AAT | GTC | ACT | GTT | GGG | GAT | TTT | TTC | AGC | 4483 |
| Asp | Phe | Ala | Leu | Leu | Arg | Gly | Asn | Val | Thr | Val | Gly | Asp | Phe | Phe | Ser |      |
|     |     |     |     | 145 |     |     |     |     | 150 |     |     |     |     | 155 |     |      |
| ACT | GCC | CGC | ATT | GGC | GAA | AAT | TTT | GGT | ATG | CGT | GGT | TTG | CGT | ATT | GCC | 4531 |
| Thr | Ala | Arg | Ile | Gly | Glu | Asn | Phe | Gly | Met | Arg | Gly | Leu | Arg | Ile | Ala |      |
|     |     |     | 160 |     |     |     |     | 165 |     |     |     |     | 170 |     |     |      |
| TCT | GAT | GAT | AGA | ATG | CTT | GCC | CCA | TCA | CAA | CGT | GGT | TTT | GCC | CCA | GTG | 4579 |
| Ser | Asp | Asp | Arg | Met | Leu | Ala | Pro | Ser | Gln | Arg | Gly | Phe | Ala | Pro | Val |      |
|     |     | 175 |     |     |     |     | 180 |     |     |     |     | 185 |     |     |     |      |
| GTG | CGT | GGC | GTG | GCA | AAC | ACA | AAC | GCC | AAA | GTC | AGC | ATC | AAA | CAA | AAT | 4627 |
| Val | Arg | Gly | Val | Ala | Asn | Thr | Asn | Ala | Lys | Val | Ser | Ile | Lys | Gln | Asn |      |
|     | 190 |     |     |     |     | 195 |     |     |     |     | 200 |     |     |     |     |      |
| GGC | TAT | ACG | ATT | TAT | CAA | ATC | ACC | GTT | CCC | GCA | GGG | CCT | TTC | GTG | ATT | 4675 |
| Gly | Tyr | Thr | Ile | Tyr | Gln | Ile | Thr | Val | Pro | Ala | Gly | Pro | Phe | Val | Ile |      |
| 205 |     |     |     |     | 210 |     |     |     |     | 215 |     |     |     |     | 220 |      |
| AAC | GAT | TTG | TAT | GCC | AGC | GGT | TAT | AGC | GGC | GAT | TTA | ACG | GTG | GAA | ATC | 4723 |
| Asn | Asp | Leu | Tyr | Ala | Ser | Gly | Tyr | Ser | Gly | Asp | Leu | Thr | Val | Glu | Ile |      |
|     |     |     |     | 225 |     |     |     |     | 230 |     |     |     |     | 235 |     |      |
| CAA | GAA | AGT | GAT | GGT | AAA | GTG | CGG | TCA | TTT | ATT | GTG | CCG | TTT | TCT | AAT | 4771 |
| Gln | Glu | Ser | Asp | Gly | Lys | Val | Arg | Ser | Phe | Ile | Val | Pro | Phe | Ser | Asn |      |
|     |     |     | 240 |     |     |     |     | 245 |     |     |     |     | 250 |     |     |      |
| CTT | GCC | CCG | TTA | ATG | CGT | GTG | GGG | CAT | TTG | CGT | TAT | CAA | TTA | GCT | GGC | 4819 |
| Leu | Ala | Pro | Leu | Met | Arg | Val | Gly | His | Leu | Arg | Tyr | Gln | Leu | Ala | Gly |      |
|     |     | 255 |     |     |     |     | 260 |     |     |     |     | 265 |     |     |     |      |
| GGA | CGT | TAT | CGA | ATT | GAC | AGC | CGC | ACC | TTT | GAT | GAA | CGT | GTG | TTA | CAA | 4867 |
| Gly | Arg | Tyr | Arg | Ile | Asp | Ser | Arg | Thr | Phe | Asp | Glu | Arg | Val | Leu | Gln |      |
|     | 270 |     |     |     |     | 275 |     |     |     |     | 280 |     |     |     |     |      |
| GGC | GTG | TTG | CAA | TAT | GGT | TTA | ACT | AAT | CAT | CTC | ACG | CTG | AAT | TCA | AGC | 4915 |
| Gly | Val | Leu | Gln | Tyr | Gly | Leu | Thr | Asn | His | Leu | Thr | Leu | Asn | Ser | Ser |      |
| 285 |     |     |     |     | 290 |     |     |     |     | 295 |     |     |     |     | 300 |      |
| CTG | CTT | TAT | ACA | CGT | CAT | TAT | CGT | GCA | GGG | CTG | TTT | GGT | TTT | GGT | TTA | 4963 |
| Leu | Leu | Tyr | Thr | Arg | His | Tyr | Arg | Ala | Gly | Leu | Phe | Gly | Phe | Gly | Leu |      |
|     |     |     |     | 305 |     |     |     |     | 310 |     |     |     |     | 315 |     |      |
| AAT | ACG | CCG | ATT | GGG | GCG | TTT | TCT | GCT | GAT | GCC | ACT | TGG | TCG | CAC | GCT | 5011 |
| Asn | Thr | Pro | Ile | Gly | Ala | Phe | Ser | Ala | Asp | Ala | Thr | Trp | Ser | His | Ala |      |
|     |     |     | 320 |     |     |     |     | 325 |     |     |     |     | 330 |     |     |      |
| GAA | TTT | CCG | CTA | AAA | CAT | GTG | AGC | AAA | AAC | GGC | TAC | AGC | TTG | CAC | GGC | 5059 |
| Glu | Phe | Pro | Leu | Lys | His | Val | Ser | Lys | Asn | Gly | Tyr | Ser | Leu | His | Gly |      |
|     |     | 335 |     |     |     |     | 340 |     |     |     |     | 345 |     |     |     |      |
| AGT | TAT | AGT | ATT | AAC | TTC | AAT | GAA | AGT | GGC | ACC | AAT | ATC | ACG | TTG | GCA | 5107 |
| Ser | Tyr | Ser | Ile | Asn | Phe | Asn | Glu | Ser | Gly | Thr | Asn | Ile | Thr | Leu | Ala |      |
|     | 350 |     |     |     |     | 355 |     |     |     |     | 360 |     |     |     |     |      |
| GCC | TAT | CGC | TAT | TCT | TCA | CGG | GAT | TTT | TAC | ACC | TTA | AGC | GAC | ACC | ATT | 5155 |
| Ala | Tyr | Arg | Tyr | Ser | Ser | Arg | Asp | Phe | Tyr | Thr | Leu | Ser | Asp | Thr | Ile |      |
| 365 |     |     |     |     | 370 |     |     |     |     | 375 |     |     |     |     | 380 |      |
| GGT | CTT | AAC | CGC | ACT | TTC | AGA | CAA | TTT | AGC | GGT | GCG | TAT | TTG | CCT | GAA | 5203 |
| Gly | Leu | Asn | Arg | Thr | Phe | Arg | Gln | Phe | Ser | Gly | Ala | Tyr | Leu | Pro | Glu |      |
|     |     |     |     | 385 |     |     |     |     | 390 |     |     |     |     | 395 |     |      |
| ATT | TAC | CGC | CCA | AAA | AAT | CAG | TTT | CAA | GTG | AGT | TTA | AGC | CAA | AGT | CTG | 5251 |
| Ile | Tyr | Arg | Pro | Lys | Asn | Gln | Phe | Gln | Val | Ser | Leu | Ser | Gln | Ser | Leu |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 400 |     |     |     |     |     | 405 |     |     |     |     |     | 410 |      |
| GGG | AAT | TGG | GGA | AAT | CTC | TAT | CTT | TCA | GGA | CAA | ACC | TAT | AAT | TAT | TGG | 5299 |
| Gly | Asn | Trp | Gly | Asn | Leu | Tyr | Leu | Ser | Gly | Gln | Thr | Tyr | Asn | Tyr | Trp |      |
|     |     | 415 |     |     |     |     | 420 |     |     |     |     | 425 |     |     |     |      |
| GAA | AAA | CGT | GGC | ACG | AAT | ACG | CAA | TAT | CAA | GTT | GCC | TAT | TCA | AAC | AGC | 5347 |
| Glu | Lys | Arg | Gly | Thr | Asn | Thr | Gln | Tyr | Gln | Val | Ala | Tyr | Ser | Asn | Ser |      |
|     | 430 |     |     |     |     | 435 |     |     |     |     | 440 |     |     |     |     |      |
| TTC | CAC | ATT | CTT | AAT | TAC | TCT | GTA | AAC | CTC | TCA | CAG | AGT | ATT | GAT | AAA | 5395 |
| Phe | His | Ile | Leu | Asn | Tyr | Ser | Val | Asn | Leu | Ser | Gln | Ser | Ile | Asp | Lys |      |
| 445 |     |     |     |     | 450 |     |     |     |     | 455 |     |     |     |     | 460 |      |
| GAA | ACG | GGC | AAA | CGT | GAC | AAC | AGC | ATT | TAT | TTA | AGT | CTC | AGC | CTG | CCA | 5443 |
| Glu | Thr | Gly | Lys | Arg | Asp | Asn | Ser | Ile | Tyr | Leu | Ser | Leu | Ser | Leu | Pro |      |
|     |     |     |     | 465 |     |     |     |     | 470 |     |     |     |     | 475 |     |      |
| TTA | GGC | GAT | AAC | CAT | TCT | GCA | GAT | AGT | AGT | TAT | TCT | CGC | AGT | GGT | AAC | 5491 |
| Leu | Gly | Asp | Asn | His | Ser | Ala | Asp | Ser | Ser | Tyr | Ser | Arg | Ser | Gly | Asn |      |
|     |     |     | 480 |     |     |     |     | 485 |     |     |     |     | 490 |     |     |      |
| GAT | ATT | AAC | CAA | CGA | CTT | GGC | GTA | AAT | GGC | TCT | TTT | GGT | GAA | CGT | CAT | 5539 |
| Asp | Ile | Asn | Gln | Arg | Leu | Gly | Val | Asn | Gly | Ser | Phe | Gly | Glu | Arg | His |      |
|     |     | 495 |     |     |     |     | 500 |     |     |     |     | 505 |     |     |     |      |
| CAA | TGG | AGT | TAT | GGT | ATT | AAC | GCT | TCA | CGC | AAT | AAT | CAA | GGC | TAT | CGC | 5587 |
| Gln | Trp | Ser | Tyr | Gly | Ile | Asn | Ala | Ser | Arg | Asn | Asn | Gln | Gly | Tyr | Arg |      |
|     | 510 |     |     |     |     | 515 |     |     |     |     | 520 |     |     |     |     |      |
| AGT | TAT | GAC | GGT | AAT | CTT | TCG | CAT | AAC | AAT | AGC | ATT | GGT | AGT | TAC | CGT | 5635 |
| Ser | Tyr | Asp | Gly | Asn | Leu | Ser | His | Asn | Asn | Ser | Ile | Gly | Ser | Tyr | Arg |      |
| 525 |     |     |     |     | 530 |     |     |     |     | 535 |     |     |     |     | 540 |      |
| GCT | TCT | TAT | TCA | CGT | GAT | AGC | CTC | AAA | AAT | CGC | TCC | ATC | TCA | CTG | GGC | 5683 |
| Ala | Ser | Tyr | Ser | Arg | Asp | Ser | Leu | Lys | Asn | Arg | Ser | Ile | Ser | Leu | Gly |      |
|     |     |     |     | 545 |     |     |     |     | 550 |     |     |     |     | 555 |     |      |
| GCA | AGC | GGT | GCT | GTC | GTG | GCG | CAC | AAA | CAC | GGT | ATT | ACC | TTA | AGC | CAA | 5731 |
| Ala | Ser | Gly | Ala | Val | Val | Ala | His | Lys | His | Gly | Ile | Thr | Leu | Ser | Gln |      |
|     |     |     | 560 |     |     |     |     | 565 |     |     |     |     | 570 |     |     |      |
| CCT | GTT | GGC | GAA | AGT | TTT | GCC | ATT | ATT | CAC | GCC | AAA | GAT | GCC | GCA | GGA | 5779 |
| Pro | Val | Gly | Glu | Ser | Phe | Ala | Ile | Ile | His | Ala | Lys | Asp | Ala | Ala | Gly |      |
|     |     | 575 |     |     |     |     | 580 |     |     |     |     | 585 |     |     |     |      |
| GCA | AAA | GTG | GAA | TCA | GGT | GCC | AAT | GTG | AGC | CTT | GAT | TAT | TTC | GGC | AAT | 5827 |
| Ala | Lys | Val | Glu | Ser | Gly | Ala | Asn | Val | Ser | Leu | Asp | Tyr | Phe | Gly | Asn |      |
|     | 590 |     |     |     |     | 595 |     |     |     |     | 600 |     |     |     |     |      |
| GCG | GTT | ATG | CCT | TAC | ACC | AGC | CCG | TAT | GAA | ATC | AAT | TAT | ATC | GGT | ATC | 5875 |
| Ala | Val | Met | Pro | Tyr | Thr | Ser | Pro | Tyr | Glu | Ile | Asn | Tyr | Ile | Gly | Ile |      |
| 605 |     |     |     |     | 610 |     |     |     |     | 615 |     |     |     |     | 620 |      |
| AAT | CCA | TCT | GAT | GCG | GAG | GCG | AAT | GTG | GAA | TTT | GAA | GCC | ACT | GAA | CGC | 5923 |
| Asn | Pro | Ser | Asp | Ala | Glu | Ala | Asn | Val | Glu | Phe | Glu | Ala | Thr | Glu | Arg |      |
|     |     |     |     | 625 |     |     |     |     | 630 |     |     |     |     | 635 |     |      |
| CAA | ATC | ATT | CCT | CGT | GCA | AAT | TCA | ATT | AGC | TTA | GTA | GAT | TTC | CGC | ACG | 5971 |
| Gln | Ile | Ile | Pro | Arg | Ala | Asn | Ser | Ile | Ser | Leu | Val | Asp | Phe | Arg | Thr |      |
|     |     |     | 640 |     |     |     |     | 645 |     |     |     |     | 650 |     |     |      |
| GGC | AAA | AAT | ACA | ATG | GTG | TTA | TTT | AAC | CTC | ACT | TTG | CCA | AAT | GGC | GAG | 6019 |
| Gly | Lys | Asn | Thr | Met | Val | Leu | Phe | Asn | Leu | Thr | Leu | Pro | Asn | Gly | Glu |      |
|     |     | 655 |     |     |     |     | 660 |     |     |     |     | 665 |     |     |     |      |
| CCA | GTG | CCA | ATG | GCA | TCC | ACC | GCA | CAA | GAT | AGC | GAA | GGG | GCA | TTT | GTG | 6067 |
| Pro | Val | Pro | Met | Ala | Ser | Thr | Ala | Gln | Asp | Ser | Glu | Gly | Ala | Phe | Val |      |
|     |     | 670 |     |     |     |     | 675 |     |     |     |     | 680 |     |     |     |      |
| GGC | GAT | GTG | GTG | CAA | GGT | GGT | GTG | CTT | TTC | GCT | AAT | AAA | CTT | ACC | CAG | 6115 |
| Gly | Asp | Val | Val | Gln | Gly | Gly | Val | Leu | Phe | Ala | Asn | Lys | Leu | Thr | Gln |      |
| 685 |     |     |     |     | 690 |     |     |     |     | 695 |     |     |     |     | 700 |      |
| CCA | AAA | GGC | GAG | TTA | ATC | GTC | AAA | TGG | GGT | GAG | CGA | GAA | AGC | GAA | CAA | 6163 |
| Pro | Lys | Gly | Glu | Leu | Ile | Val | Lys | Trp | Gly | Glu | Arg | Glu | Ser | Glu | Gln |      |
|     |     |     |     | 705 |     |     |     |     | 710 |     |     |     |     | 715 |     |      |
| TGC | CGT | TTC | CAA | TAT | CAA | GTT | GAT | TTG | GAT | AAC | GCA | CAA | ATA | CAA | AGT | 6211 |
| Cys | Arg | Phe | Gln | Tyr | Gln | Val | Asp | Leu | Asp | Asn | Ala | Gln | Ile | Gln | Ser |      |

|     |     |     |     |     | 720 |     |     |     | 725 |     |     |     | 730 |     |     |      |
|-----|-----|-----|-----|-----|-----|-----|-----|-----|-----|-----|-----|-----|-----|-----|-----|------|

```
CAC GAT ATT CAA TGC AAA ACC GCA AAA TAAATAATTG AAGAGGATTT ATG                  6261
His Asp Ile Gln Cys Lys Thr Ala Lys                             Met
        735             740                                     1

CAA AAA ACA CCC AAA AAA TTA ACC GCG CTT TTC CAT CAA AAA TCC ACT                6309
Gln Lys Thr Pro Lys Lys Leu Thr Ala Leu Phe His Gln Lys Ser Thr
            5               10              15

GCT ACT TGT AGT GGA GCA AAT TAT AGT GGA GCA AAT TAT AGT GGC TCA                6357
Ala Thr Cys Ser Gly Ala Asn Tyr Ser Gly Ala Asn Tyr Ser Gly Ser
        20              25              30

AAA TGC TTT AGG TTT CAT CGT CTG GCT CTG CTT GCT TGC GTG GCT CTG                6405
Lys Cys Phe Arg Phe His Arg Leu Ala Leu Leu Ala Cys Val Ala Leu
    35              40                  45

CTT GAT TGC ATT GTG GCA CTG CCT GCT TAT GCT TAC GAT GGC AGA GTG                6453
Leu Asp Cys Ile Val Ala Leu Pro Ala Tyr Ala Tyr Asp Gly Arg Val
50              55                  60                      65

ACC TTT CAA GGG GAG ATT TTA AGT GAT GGC ACT TGT AAA ATT GAA ACA                6501
Thr Phe Gln Gly Glu Ile Leu Ser Asp Gly Thr Cys Lys Ile Glu Thr
                    70              75              80

GAC AGC CAA AAT CGC ACG GTT ACC CTG CCA ACA GTG GGA AAA GCT AAT                6549
Asp Ser Gln Asn Arg Thr Val Thr Leu Pro Thr Val Gly Lys Ala Asn
            85              90              95

TTA AGC CAC GCA GGG CAA ACC GCC GCC CCT GTG CCT TTT TCC ATC ACG                6597
Leu Ser His Ala Gly Gln Thr Ala Ala Pro Val Pro Phe Ser Ile Thr
            100             105             110

TTA AAA GAA TGC AAT GCA GAT GAT GCT ATG AAA GCT AAT CTG CTA TTT                6645
Leu Lys Glu Cys Asn Ala Asp Asp Ala Met Lys Ala Asn Leu Leu Phe
    115             120             125

AAA GGG GGA GAC AAC ACA ACA GGG CAA TCT TAT CTT TCC AAT AAG GCA                6693
Lys Gly Gly Asp Asn Thr Thr Gly Gln Ser Tyr Leu Ser Asn Lys Ala
130             135             140                     145

GGC AAC GGC AAA GCC ACC AAC GTG GGC ATT CAA ATT GTC AAA GCC GAT                6741
Gly Asn Gly Lys Ala Thr Asn Val Gly Ile Gln Ile Val Lys Ala Asp
                150             155                 160

GGC ATA GGC ACG CCT ATC AAG GTG GAC GGC ACC GAA GCC AAC AGC GAA                6789
Gly Ile Gly Thr Pro Ile Lys Val Asp Gly Thr Glu Ala Asn Ser Glu
        165             170             175

AAA GCC CCC GAC ACA GGT AAA GCG CAA AAC GGC ACA GTT ATT CAA CCC                6837
Lys Ala Pro Asp Thr Gly Lys Ala Gln Asn Gly Thr Val Ile Gln Pro
        180             185             190

CGT TTT GGC TAC TTT GGC TCG TTA TTA CGC CAC AGG TGAAGCCACC                     6883
Arg Phe Gly Tyr Phe Gly Ser Leu Leu Arg His Arg
    195             200             205

GCAGGCGACG TTGAAGCCAC TGCAACTTTT GAAGTGCAGT ATAACTAAAA TATTTATTAT              6943

CCAGTGAAAA A ATG AAT AAG AAA TCG TAT ATA AAT CAT TAC TTA ACT TTA               6993
             Met Asn Lys Lys Ser Tyr Ile Asn His Tyr Leu Thr Leu
             1               5               10

TTT AAA GTT ACT ACT TTA CTA TTT ACT CTT TCA AGT AAT CCT GTA TGG                7041
Phe Lys Val Thr Thr Leu Leu Phe Thr Leu Ser Ser Asn Pro Val Trp
        15              20              25

GCA AAT ATA AAA ACA GTT CAG GGA ACA ACT AGT GGT TTT CCA CTT CTA                7089
Ala Asn Ile Lys Thr Val Gln Gly Thr Thr Ser Gly Phe Pro Leu Leu
30              35              40                      45

ACA AGA ACT TTC ACA TTT AAT GGC AAT TTG CAA TGG AAT GTG AGT GCT                7137
Thr Arg Thr Phe Thr Phe Asn Gly Asn Leu Gln Trp Asn Val Ser Ala
                50              55              60

CTA CAA CCA GCT TAT ATT GTT TCC TCT CAA GCA AGA GAT AAT CTT GAT                7185
Leu Gln Pro Ala Tyr Ile Val Ser Ser Gln Ala Arg Asp Asn Leu Asp
        65              70              75
```

-continued

| | | | | | | | | | | | | | | | | |
|---|---|---|---|---|---|---|---|---|---|---|---|---|---|---|---|---|
| ACA | GTA | CAT | ATT | CAA | TCT | TCT | GAA | ATT | AAT | GCT | CCA | ACA | AAT | TCA | TTA | 7233 |
| Thr | Val | His | Ile | Gln | Ser | Ser | Glu | Ile | Asn | Ala | Pro | Thr | Asn | Ser | Leu | |
| | | 80 | | | | | 85 | | | | | 90 | | | | |
| GCT | CCA | TTT | AAT | AAT | TGG | ATT | AAT | ACG | AAA | TCA | GCA | GTA | GAG | CTA | GGT | 7281 |
| Ala | Pro | Phe | Asn | Asn | Trp | Ile | Asn | Thr | Lys | Ser | Ala | Val | Glu | Leu | Gly | |
| | 95 | | | | | 100 | | | | | 105 | | | | | |
| TAT | AGC | TTT | GCG | GGC | ATT | ACT | TGT | ACT | AGT | AAT | CCT | TGC | CCA | ACA | ATG | 7329 |
| Tyr | Ser | Phe | Ala | Gly | Ile | Thr | Cys | Thr | Ser | Asn | Pro | Cys | Pro | Thr | Met | |
| 110 | | | | | 115 | | | | | 120 | | | | | 125 | |
| AAA | TTA | CCA | TTA | TTA | TTT | CAT | CCT | GAT | CTT | ACT | AAT | TTA | ACT | CCA | CCT | 7377 |
| Lys | Leu | Pro | Leu | Leu | Phe | His | Pro | Asp | Leu | Thr | Asn | Leu | Thr | Pro | Pro | |
| | | | | 130 | | | | | 135 | | | | | 140 | | |
| GGA | AAG | AAA | AAT | TCT | GAT | GGA | GGG | GAG | ATT | TTT | AAA | TTA | CAT | AAT | GAA | 7425 |
| Gly | Lys | Lys | Asn | Ser | Asp | Gly | Gly | Glu | Ile | Phe | Lys | Leu | His | Asn | Glu | |
| | | | 145 | | | | | 150 | | | | | 155 | | | |
| TCT | AAT | TTA | GGC | GTC | TCT | TTT | CAA | ATT | GGA | GTA | AAA | ACG | AAT | ACT | TCT | 7473 |
| Ser | Asn | Leu | Gly | Val | Ser | Phe | Gln | Ile | Gly | Val | Lys | Thr | Asn | Thr | Ser | |
| | | 160 | | | | | 165 | | | | | 170 | | | | |
| CTA | GAT | TGG | GTT | AAT | GCT | AAG | AAT | AAT | TTT | AGC | TCT | CTA | AAA | GTT | TTA | 7521 |
| Leu | Asp | Trp | Val | Asn | Ala | Lys | Asn | Asn | Phe | Ser | Ser | Leu | Lys | Val | Leu | |
| | 175 | | | | | 180 | | | | | 185 | | | | | |
| ATG | GTG | CCT | TTT | AAT | TCT | AGC | GAT | AAA | ATA | TCT | TTG | CAT | TTA | CGT | GCT | 7569 |
| Met | Val | Pro | Phe | Asn | Ser | Ser | Asp | Lys | Ile | Ser | Leu | His | Leu | Arg | Ala | |
| 190 | | | | | 195 | | | | | 200 | | | | | 205 | |
| AAA | TTT | CAT | TTA | TTA | ACA | GAT | TTT | TCA | TCG | CTA | AAT | AAT | GAT | ATT | ACT | 7617 |
| Lys | Phe | His | Leu | Leu | Thr | Asp | Phe | Ser | Ser | Leu | Asn | Asn | Asp | Ile | Thr | |
| | | | | 210 | | | | | 215 | | | | | 220 | | |
| ATT | GAC | CCT | ATG | AAT | ACT | AGT | ATA | GGC | AAA | ATT | AAT | CTT | GAA | ACG | TGG | 7665 |
| Ile | Asp | Pro | Met | Asn | Thr | Ser | Ile | Gly | Lys | Ile | Asn | Leu | Glu | Thr | Trp | |
| | | | 225 | | | | | 230 | | | | | 235 | | | |
| CGT | GGC | TCA | ACA | GGC | AAT | TTT | TCT | GTT | AAA | TAT | GTA | GGT | GAG | GAT | AAG | 7713 |
| Arg | Gly | Ser | Thr | Gly | Asn | Phe | Ser | Val | Lys | Tyr | Val | Gly | Glu | Asp | Lys | |
| | | 240 | | | | | 245 | | | | | 250 | | | | |
| GGA | GAT | ATA | TCT | ATT | TTC | TTT | AAT | ACA | CCT | AAA | ATT | ATT | CTA | AAA | AAA | 7761 |
| Gly | Asp | Ile | Ser | Ile | Phe | Phe | Asn | Thr | Pro | Lys | Ile | Ile | Leu | Lys | Lys | |
| | 255 | | | | | 260 | | | | | 265 | | | | | |
| CAA | CAA | CGC | CGA | TGT | ACT | CTG | AAT | AAT | GCT | CCA | GTG | AGC | CCA | AAT | CCA | 7809 |
| Gln | Gln | Arg | Arg | Cys | Thr | Leu | Asn | Asn | Ala | Pro | Val | Ser | Pro | Asn | Pro | |
| 270 | | | | | 275 | | | | | 280 | | | | | 285 | |
| GTT | AAA | TTA | CGA | GCG | GTA | AAA | AAA | CGT | GAA | TTG | GAG | GCA | CAA | AGT | GAA | 7857 |
| Val | Lys | Leu | Arg | Ala | Val | Lys | Lys | Arg | Glu | Leu | Glu | Ala | Gln | Ser | Glu | |
| | | | | 290 | | | | | 295 | | | | | 300 | | |
| ATG | GAA | GGT | GGG | ACA | TTT | CAG | TTA | AGA | GTA | AAT | TGT | GAC | AAT | ACC | ACT | 7905 |
| Met | Glu | Gly | Gly | Thr | Phe | Gln | Leu | Arg | Val | Asn | Cys | Asp | Asn | Thr | Thr | |
| | | | 305 | | | | | 310 | | | | | 315 | | | |
| TAT | AAT | AAA | GCC | AAC | GGC | AAA | TGG | TTA | TTT | CCT | GTA | GTG | AAA | GTT | ACT | 7953 |
| Tyr | Asn | Lys | Ala | Asn | Gly | Lys | Trp | Leu | Phe | Pro | Val | Val | Lys | Val | Thr | |
| | | 320 | | | | | 325 | | | | | 330 | | | | |
| TTT | ACG | GAC | GAA | GAT | GGT | ACA | ACG | AAT | AAT | GGA | ACA | AAT | GAC | TTA | CTT | 8001 |
| Phe | Thr | Asp | Glu | Asp | Gly | Thr | Thr | Asn | Asn | Gly | Thr | Asn | Asp | Leu | Leu | |
| | 335 | | | | | 340 | | | | | 345 | | | | | |
| CGC | ACC | CAA | ACA | GGC | AGC | GGA | CAA | GCC | ACA | GGC | GTT | AGC | TTA | AGA | ATC | 8049 |
| Arg | Thr | Gln | Thr | Gly | Ser | Gly | Gln | Ala | Thr | Gly | Val | Ser | Leu | Arg | Ile | |
| 350 | | | | | 355 | | | | | 360 | | | | | 365 | |
| AAA | CGA | GAA | AAT | GGT | ACA | GAA | ACC | GTA | AAA | TAC | GGT | GCT | GAT | TCT | GCT | 8097 |
| Lys | Arg | Glu | Asn | Gly | Thr | Glu | Thr | Val | Lys | Tyr | Gly | Ala | Asp | Ser | Ala | |
| | | | | 370 | | | | | 375 | | | | | 380 | | |
| CAA | ATG | GGG | AAT | GCT | GGA | CAA | TTT | GAA | TTA | CGA | AAA | CAA | CCA | TCC | CCT | 8145 |
| Gln | Met | Gly | Asn | Ala | Gly | Gln | Phe | Glu | Leu | Arg | Lys | Gln | Pro | Ser | Pro | |
| | | | 385 | | | | | 390 | | | | | 395 | | | |

| | | | | | | | | | | | | | | | | |
|---|---|---|---|---|---|---|---|---|---|---|---|---|---|---|---|---|
| GCT | GGT | GGA | GAT | CAA | TAT | GCT | GAA | GAA | ACT | TTC | AAA | GTC | TAT | TAC | GTA | 8193 |
| Ala | Gly | Gly | Asp | Gln | Tyr | Ala | Glu | Glu | Thr | Phe | Lys | Val | Tyr | Tyr | Val | |
| | | 400 | | | | 405 | | | | | 410 | | | | | |
| AAA | GAC | TCA | ACA | AGA | GGC | ACC | TTA | ATC | GAA | GGA | AAA | GTC | AAA | GCC | GCC | 8241 |
| Lys | Asp | Ser | Thr | Arg | Gly | Thr | Leu | Ile | Glu | Gly | Lys | Val | Lys | Ala | Ala | |
| | | 415 | | | | 420 | | | | | 425 | | | | | |
| GCC | ACT | TTC | ACA | ATG | TCA | TAT | CAA | TAATAATGTC | | GGGTGGGAAT | | ATAAAGGCTG | | | | 8295 |
| Ala | Thr | Phe | Thr | Met | Ser | Tyr | Gln | | | | | | | | | |
| 430 | | | | | 435 | | | | | | | | | | | |

AAGGTTTAAA CTTCAGTCTT TTTTTATAGG AAAATACCAT TGCAACTTTA AGGATAAAAT   8355

| | | | | | | | | | | | |
|---|---|---|---|---|---|---|---|---|---|---|---|
| TTTATCCTAA | GCACAATTTT | TATAAGAATA | GGTCAAATT | ATG | TTA | GCC | AAA | GCA | | | 8409 |
| | | | | Met | Leu | Ala | Lys | Ala | | | |
| | | | | 1 | | | | 5 | | | |
| AAA | TAT | AGA | AAA | GAT | TAC | AAA | CAA | CCA | GAT | TTT | ACG | GTC | ACA | GAC | ATT | 8457 |
| Lys | Tyr | Arg | Lys | Asp | Tyr | Lys | Gln | Pro | Asp | Phe | Thr | Val | Thr | Asp | Ile | |
| | | | 10 | | | | 15 | | | | 20 | | | | | |
| TAT | TTA | GAT | TTT | CAA | CTT | GAT | CCT | AAA | AAT | ACT | GTG | GTG | ACT | GCA | ACC | 8505 |
| Tyr | Leu | Asp | Phe | Gln | Leu | Asp | Pro | Lys | Asn | Thr | Val | Val | Thr | Ala | Thr | |
| | | | 25 | | | | 30 | | | | 35 | | | | | |
| ACA | AAA | TTC | CAA | CGC | TTA | AAT | AAT | GAA | GCG | ACG | TCT | TTA | CGT | TTA | GAC | 8553 |
| Thr | Lys | Phe | Gln | Arg | Leu | Asn | Asn | Glu | Ala | Thr | Ser | Leu | Arg | Leu | Asp | |
| | | 40 | | | | 45 | | | | | 50 | | | | | |
| GGG | CAT | AGC | TTC | CAG | TTT | TCT | TCT | ATT | AAA | TTT | AAT | GGC | GAG | CCA | TTT | 8601 |
| Gly | His | Ser | Phe | Gln | Phe | Ser | Ile | Lys | Phe | Asn | Gly | Glu | Pro | Phe | | |
| | 55 | | | | | 60 | | | | | 65 | | | | | |
| TCT | GAT | TAT | CAA | CAA | GAT | GGC | GAG | AGT | TTA | ACG | CTC | GAT | TTA | AAA | GAC | 8649 |
| Ser | Asp | Tyr | Gln | Gln | Asp | Gly | Glu | Ser | Leu | Thr | Leu | Asp | Leu | Lys | Asp | |
| 70 | | | | | 75 | | | | | 80 | | | | | 85 | |
| AAA | AGT | GCG | GAT | GAA | TTT | GAG | CTT | GAA | ATT | GTG | ACG | TTC | CTT | GTG | CCA | 8697 |
| Lys | Ser | Ala | Asp | Glu | Phe | Glu | Leu | Glu | Ile | Val | Thr | Phe | Leu | Val | Pro | |
| | | | | 90 | | | | 95 | | | | | 100 | | | |
| GCC | GAA | AAT | ACG | TCA | TTA | CAA | GGG | CTA | TAT | CAG | TCT | GGC | GAA | GGT | ATT | 8745 |
| Ala | Glu | Asn | Thr | Ser | Leu | Gln | Gly | Leu | Tyr | Gln | Ser | Gly | Glu | Gly | Ile | |
| | | | 105 | | | | 110 | | | | | 115 | | | | |
| TGT | ACG | CAA | TGT | GAG | GCG | GAA | GGT | TTC | CGT | CAA | ATC | ACT | TAT | ATG | CTT | 8793 |
| Cys | Thr | Gln | Cys | Glu | Ala | Glu | Gly | Phe | Arg | Gln | Ile | Thr | Tyr | Met | Leu | |
| | | 120 | | | | | 125 | | | | | 130 | | | | |
| GAT | CGT | CCT | GAT | GTG | CTG | GCG | CGT | TAT | ATA | ATC | AAA | ATT | ACG | GCA | GAT | 8841 |
| Asp | Arg | Pro | Asp | Val | Leu | Ala | Arg | Tyr | Ile | Ile | Lys | Ile | Thr | Ala | Asp | |
| | 135 | | | | 140 | | | | | 145 | | | | | | |
| AAA | ACC | AAA | TAT | CCA | TTC | TTA | CTG | TCG | AAT | GGT | AAT | CGC | ATT | GCA | AGT | 8889 |
| Lys | Thr | Lys | Tyr | Pro | Phe | Leu | Leu | Ser | Asn | Gly | Asn | Arg | Ile | Ala | Ser | |
| 150 | | | | | 155 | | | | | 160 | | | | | 165 | |
| GGC | GAA | TTA | GAA | GAT | GGT | CGC | CAT | TGG | GTG | GAA | TGG | AAT | GAT | CCT | TTC | 8937 |
| Gly | Glu | Leu | Glu | Asp | Gly | Arg | His | Trp | Val | Glu | Trp | Asn | Asp | Pro | Phe | |
| | | | | 170 | | | | 175 | | | | | 180 | | | |
| CCA | AAA | CCA | AGC | TAT | TTA | TTT | GCT | TTA | GTG | GCG | GGA | GAT | TNN | GGT | TTA | 8985 |
| Pro | Lys | Pro | Ser | Tyr | Leu | Phe | Ala | Leu | Val | Ala | Gly | Asp | Xaa | Gly | Leu | |
| | | | 185 | | | | 190 | | | | | 195 | | | | |
| TTA | CAA | GAT | AAN | TTT | ATT | ACT | AAA | AGT | GGT | CGT | GAA | GTG | GCT | TTA | GAG | 9033 |
| Leu | Gln | Asp | Xaa | Phe | Ile | Thr | Lys | Ser | Gly | Arg | Glu | Val | Ala | Leu | Glu | |
| | | | 200 | | | | 205 | | | | | 210 | | | | |
| CTT | TAT | GTG | GAT | CGC | GGT | AAT | CTT | AAC | CGT | GCA | ACT | GGG | GCA | ATG | GAA | 9081 |
| Leu | Tyr | Val | Asp | Arg | Gly | Asn | Leu | Asn | Arg | Ala | Thr | Gly | Ala | Met | Glu | |
| | 215 | | | | | 220 | | | | | 225 | | | | | |
| AGT | CTG | AAA | AAA | GCG | ATG | AAA | TGG | GAT | GAA | GAT | CGC | TTT | ATT | TTA | GAA | 9129 |
| Ser | Leu | Lys | Lys | Ala | Met | Lys | Trp | Asp | Glu | Asp | Arg | Phe | Ile | Leu | Glu | |
| 230 | | | | | 235 | | | | | 240 | | | | | 245 | |
| TTT | TAC | CTA | GAT | ATT | TAT | ATG | ATC | GCG | GCC | GCC | GAT | TCC | TCC | AAT | ATG | 9177 |
| Phe | Tyr | Leu | Asp | Ile | Tyr | Met | Ile | Ala | Ala | Ala | Asp | Ser | Ser | Asn | Met | |

```
                           250                          255                          260
GGC  GCA  ATG  GAA  AAT  AAA  GGA  TTA  AAT  ATC  TTT  AAC  TCT  AAA  TTG  GTG              9225
Gly  Ala  Met  Glu  Asn  Lys  Gly  Leu  Asn  Ile  Phe  Asn  Ser  Lys  Leu  Val
               265                      270                      275

TTG  GCA  AAT  CCA  CAA  ACG  GCA  ACA  GAT  GAA  GAT  TAT  CTT  GTC  ATT  GAA              9273
Leu  Ala  Asn  Pro  Gln  Thr  Ala  Thr  Asp  Glu  Asp  Tyr  Leu  Val  Ile  Glu
               280                      285                      290

AGT  GTG  ATT  GCA  CAC  GAA  TAT  TCC  CAT  AAC  TGG  ACG  GGA  AAC  CGT  GTA              9321
Ser  Val  Ile  Ala  His  Glu  Tyr  Ser  His  Asn  Trp  Thr  Gly  Asn  Arg  Val
     295                      300                      305

ACC  CGC  CGA  GAT  GGG  TTC  AACTAGGTTT  GAAGAAGGTT  AACGGCTTCC                             9369
Thr  Arg  Arg  Asp  Gly  Phe
310                 315

GGGAACAAGA  TTTCTCAGAT  CAGTTCTCCG  GGCCGGAACC  GATTAATAAG  GGAAAATTTT                      9429

CCG                                                                                          9432
```

( 2 ) INFORMATION FOR SEQ ID NO:2:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Gln  Phe  Ile  Met  Lys  Lys  Thr  Leu  Leu  Gly  Ser  Leu  Ile  Leu
 1                    5                    10                       15

Leu  Ala  Phe  Ala  Thr  Asn  Ala  Ala  Asp  Pro  Gln  Val  Ser  Thr  Glu  Thr
               20                       25                       30

Ser  Gly  Lys  Val  Thr  Phe  Phe  Gly  Lys  Val  Val  Glu  Asn  Thr  Cys  Lys
          35                       40                       45

Val  Lys  Thr  Asp  Ser  Lys  Asn  Met  Ser  Val  Val  Leu  Asn  Asp  Val  Gly
     50                       55                       60

Lys  Asn  His  Leu  Lys  Thr  Lys  Lys  Asp  Thr  Ala  Met  Pro  Thr  Pro  Phe
65                       70                       75                       80

Thr  Ile  Asn  Leu  Glu  Asn  Cys  Ser  Thr  Thr  Thr  Thr  Asn  Asn  Lys
                    85                       90                       95

Pro  Val  Ala  Thr  Lys  Val  Gly  Ala  Tyr  Phe  Tyr  Ser  Trp  Lys  Asn  Ala
               100                      105                      110

Asp  Glu  Asn  Asn  Glu  Tyr  Thr  Leu  Lys  Asn  Thr  Lys  Ser  Gly  Asn  Asp
          115                      120                      125

Ala  Ala  Gln  Asn  Val  Asn  Ile  Gln  Leu  Phe  Asp  Ala  Asn  Gly  Thr  Asp
     130                      135                      140

Ala  Ile  Glu  Val  Val  Gly  Asn  Gly  Thr  Thr  Asp  Phe  Thr  His  Ser  Asn
145                      150                      155                      160

Thr  Asn  Asp  Val  Ala  Thr  Gln  Gln  Thr  Val  Asn  Lys  Asn  His  Ile  Ser
                    165                      170                      175

Gly  Lys  Ala  Thr  Ile  Asn  Gly  Glu  Asn  Asn  Val  Lys  Leu  His  Tyr  Ile
               180                      185                      190

Ala  Arg  Tyr  Tyr  Ala  Thr  Ala  Gln  Ala  Glu  Ala  Gly  Lys  Val  Glu  Ser
          195                      200                      205

Ser  Val  Asp  Phe  Gln  Ile  Ala  Tyr  Glu
     210                      215
```

( 2 ) INFORMATION FOR SEQ ID NO:3:

( i ) SEQUENCE CHARACTERISTICS:

(A) LENGTH: 259 amino acids
(B) TYPE: amino acid
(D) TOPOLOGY: linear (ii) MOLECULE TYPE: protein (xi) SEQUENCE DESCRIPTION: SEQ ID NO:3:

| Met | Asn | Lys | Asp | Lys | Tyr | Gly | Leu | Ser | Pro | Val | Tyr | Gly | Phe | Asn | Tyr |
|---|---|---|---|---|---|---|---|---|---|---|---|---|---|---|---|
| 1 | | | | 5 | | | | | 10 | | | | | 15 | |
| Val | Glu | Met | Gly | Lys | Thr | Met | Phe | Lys | Lys | Thr | Leu | Leu | Phe | Phe | Thr |
| | | | 20 | | | | | 25 | | | | | 30 | | |
| Ala | Leu | Phe | Phe | Ala | Ala | Leu | Cys | Ala | Phe | Ser | Ala | Asn | Ala | Asp | Val |
| | | | 35 | | | | 40 | | | | | 45 | | | |
| Ile | Ile | Thr | Gly | Thr | Arg | Val | Ile | Tyr | Pro | Ala | Gly | Gln | Lys | Asn | Val |
| | | 50 | | | | 55 | | | | | | 60 | | | |
| Ile | Val | Lys | Leu | Glu | Asn | Asn | Asp | Asp | Ser | Ala | Ala | Leu | Val | Gln | Ala |
| 65 | | | | | 70 | | | | | 75 | | | | | 80 |
| Trp | Ile | Asp | Asn | Gly | Asn | Pro | Asn | Ala | Asp | Pro | Lys | Tyr | Thr | Lys | Thr |
| | | | | 85 | | | | | 90 | | | | | 95 | |
| Pro | Phe | Val | Ile | Thr | Pro | Pro | Val | Ala | Arg | Val | Glu | Ala | Lys | Ser | Gly |
| | | | 100 | | | | | 105 | | | | | 110 | | |
| Gln | Ser | Leu | Arg | Ile | Thr | Phe | Thr | Gly | Ser | Glu | Pro | Leu | Pro | Asp | Asp |
| | | | 115 | | | | | 120 | | | | | 125 | | |
| Arg | Glu | Ser | Leu | Phe | Tyr | Phe | Asn | Leu | Leu | Asp | Ile | Pro | Pro | Lys | Pro |
| | 130 | | | | | 135 | | | | | 140 | | | | |
| Asp | Ala | Ala | Phe | Leu | Ala | Lys | His | Gly | Ser | Phe | Met | Gln | Ile | Ala | Ile |
| 145 | | | | | 150 | | | | | 155 | | | | | 160 |
| Arg | Ser | Arg | Leu | Lys | Leu | Phe | Tyr | Arg | Pro | Ala | Lys | Leu | Ser | Met | Asp |
| | | | | 165 | | | | | 170 | | | | | 175 | |
| Ser | Arg | Asp | Ala | Met | Lys | Lys | Val | Val | Phe | Lys | Ala | Thr | Pro | Glu | Gly |
| | | | | 180 | | | | | 185 | | | | | 190 | |
| Val | Leu | Val | Asp | Asn | Gln | Thr | Pro | Tyr | Tyr | Met | Asn | Tyr | Ile | Gly | Leu |
| | | 195 | | | | | 200 | | | | | 205 | | | |
| Leu | His | Gln | Asn | Lys | Pro | Ala | Lys | Asn | Val | Lys | Met | Val | Ala | Pro | Phe |
| | 210 | | | | | 215 | | | | | 220 | | | | |
| Ser | Gln | Ala | Val | Phe | Glu | Ala | Lys | Gly | Val | Arg | Ser | Gly | Asp | Lys | Leu |
| 225 | | | | | 230 | | | | | 235 | | | | | 240 |
| Lys | Trp | Val | Leu | Val | Asn | Asp | Tyr | Gly | Ala | Asp | Gln | Glu | Gly | Glu | Ala |
| | | | | 245 | | | | | 250 | | | | | 255 | |
| Ile | Ala | Gln | | | | | | | | | | | | | |

(2) INFORMATION FOR SEQ ID NO:4:

(i) SEQUENCE CHARACTERISTICS:
(A) LENGTH: 741 amino acids
(B) TYPE: amino acid
(D) TOPOLOGY: linear (ii) MOLECULE TYPE: protein (xi) SEQUENCE DESCRIPTION: SEQ ID NO:4:

| Met | Leu | Asp | Leu | Met | Asp | Glu | Ala | Ile | Val | Lys | Ser | Pro | Asn | Ser | Glu |
|---|---|---|---|---|---|---|---|---|---|---|---|---|---|---|---|
| 1 | | | | 5 | | | | | 10 | | | | | 15 | |
| Asp | Asp | Thr | Cys | Val | Phe | Ala | Ser | Asp | Ala | Ile | Pro | Lys | Gly | Thr | Phe |
| | | | 20 | | | | | 25 | | | | | 30 | | |
| Glu | Tyr | Gln | Ser | Gly | Glu | Met | Lys | Leu | Lys | Leu | Glu | Leu | Pro | Gln | Ala |
| | | | 35 | | | | | 40 | | | | | 45 | | |
| Leu | Thr | Ile | Arg | Arg | Pro | Arg | Gly | Tyr | Ile | Ala | Pro | Ser | Arg | Trp | Gln |

-continued

|   |   |   | 50 |   |   |   | 55 |   |   |   | 60 |   |   |   |
|---|---|---|---|---|---|---|---|---|---|---|---|---|---|---|
| Thr 65 | Gly | Thr | Asn | Ala | Ala 70 | Phe | Ala | Asn | Tyr | Asp 75 | Ile | Asn | Tyr | Tyr Arg 80 |
| Ser | Gly | Asn | Pro | Glu 85 | Val | Lys | Ser | Glu | Ser 90 | Leu | Tyr | Val | Gly | Leu Arg 95 |
| Ser | Gly | Val | Asn 100 | Phe | Gly | Asn | Trp | Ala 105 | Leu | Arg | His | Ser 110 | Gly | Ser Phe |
| Ser | Arg | Phe 115 | Glu | Asn | Gln | Ser | Ser 120 | Ser | Gly | Phe | Thr | Asp 125 | Lys | Gly Lys |
| Asn | His 130 | Tyr | Glu | Arg | Gly | Asp 135 | Thr | Tyr | Leu | Gln | Arg 140 | Asp | Phe | Ala Leu |
| Leu 145 | Arg | Gly | Asn | Val | Thr 150 | Val | Gly | Asp | Phe | Phe 155 | Ser | Thr | Ala | Arg Ile 160 |
| Gly | Glu | Asn | Phe | Gly 165 | Met | Arg | Gly | Leu | Arg 170 | Ile | Ala | Ser | Asp 175 | Asp Arg |
| Met | Leu | Ala | Pro 180 | Ser | Gln | Arg | Gly | Phe 185 | Ala | Pro | Val | Val | Arg 190 | Gly Val |
| Ala | Asn | Thr 195 | Asn | Ala | Lys | Val | Ser 200 | Ile | Lys | Gln | Asn | Gly 205 | Tyr | Thr Ile |
| Tyr | Gln 210 | Ile | Thr | Val | Pro | Ala 215 | Gly | Pro | Phe | Val | Ile 220 | Asn | Asp | Leu Tyr |
| Ala 225 | Ser | Gly | Tyr | Ser | Gly 230 | Asp | Leu | Thr | Val | Glu 235 | Ile | Gln | Glu | Ser Asp 240 |
| Gly | Lys | Val | Arg | Ser 245 | Phe | Ile | Val | Pro | Phe 250 | Ser | Asn | Leu | Ala | Pro Leu 255 |
| Met | Arg | Val | Gly 260 | His | Leu | Arg | Tyr | Gln 265 | Leu | Ala | Gly | Gly | Arg 270 | Tyr Arg |
| Ile | Asp | Ser 275 | Arg | Thr | Phe | Asp | Glu 280 | Arg | Val | Leu | Gln | Gly 285 | Val | Leu Gln |
| Tyr | Gly 290 | Leu | Thr | Asn | His | Leu 295 | Thr | Leu | Asn | Ser | Ser 300 | Leu | Leu | Tyr Thr |
| Arg 305 | His | Tyr | Arg | Ala | Gly 310 | Leu | Phe | Gly | Phe | Gly 315 | Leu | Asn | Thr | Pro Ile 320 |
| Gly | Ala | Phe | Ser | Ala 325 | Asp | Ala | Thr | Trp | Ser 330 | His | Ala | Glu | Phe | Pro Leu 335 |
| Lys | His | Val | Ser 340 | Lys | Asn | Gly | Tyr | Ser 345 | Leu | His | Gly | Ser | Tyr 350 | Ser Ile |
| Asn | Phe | Asn 355 | Glu | Ser | Gly | Thr | Asn 360 | Ile | Thr | Leu | Ala | Ala 365 | Tyr | Arg Tyr |
| Ser | Ser 370 | Arg | Asp | Phe | Tyr | Thr 375 | Leu | Ser | Asp | Thr | Ile 380 | Gly | Leu | Asn Arg |
| Thr 385 | Phe | Arg | Gln | Phe | Ser 390 | Gly | Ala | Tyr | Leu | Pro 395 | Glu | Ile | Tyr | Arg Pro 400 |
| Lys | Asn | Gln | Phe | Gln 405 | Val | Ser | Leu | Ser | Gln 410 | Ser | Leu | Gly | Asn | Trp Gly 415 |
| Asn | Leu | Tyr | Leu 420 | Ser | Gly | Gln | Thr | Tyr 425 | Asn | Tyr | Trp | Glu | Lys 430 | Arg Gly |
| Thr | Asn | Thr 435 | Gln | Tyr | Gln | Val | Ala 440 | Tyr | Ser | Asn | Ser | Phe 445 | His | Ile Leu |
| Asn | Tyr 450 | Ser | Val | Asn | Leu | Ser 455 | Gln | Ser | Ile | Asp | Lys 460 | Glu | Thr | Gly Lys |
| Arg 465 | Asp | Asn | Ser | Ile | Tyr 470 | Leu | Ser | Leu | Ser | Leu 475 | Pro | Leu | Gly | Asp Asn 480 |

| His | Ser | Ala | Asp | Ser | Ser | Tyr | Ser | Arg | Ser | Gly | Asn | Asp | Ile | Asn | Gln |
|---|---|---|---|---|---|---|---|---|---|---|---|---|---|---|---|
| | | | | 485 | | | | | 490 | | | | | 495 | |

| Arg | Leu | Gly | Val | Asn | Gly | Ser | Phe | Gly | Glu | Arg | His | Gln | Trp | Ser | Tyr |
|---|---|---|---|---|---|---|---|---|---|---|---|---|---|---|---|
| | | | 500 | | | | | 505 | | | | | 510 | | |

| Gly | Ile | Asn | Ala | Ser | Arg | Asn | Asn | Gln | Gly | Tyr | Arg | Ser | Tyr | Asp | Gly |
|---|---|---|---|---|---|---|---|---|---|---|---|---|---|---|---|
| | | 515 | | | | | 520 | | | | | 525 | | | |

| Asn | Leu | Ser | His | Asn | Asn | Ser | Ile | Gly | Ser | Tyr | Arg | Ala | Ser | Tyr | Ser |
|---|---|---|---|---|---|---|---|---|---|---|---|---|---|---|---|
| | 530 | | | | | 535 | | | | | 540 | | | | |

| Arg | Asp | Ser | Leu | Lys | Asn | Arg | Ser | Ile | Ser | Leu | Gly | Ala | Ser | Gly | Ala |
|---|---|---|---|---|---|---|---|---|---|---|---|---|---|---|---|
| 545 | | | | | 550 | | | | | 555 | | | | | 560 |

| Val | Val | Ala | His | Lys | His | Gly | Ile | Thr | Leu | Ser | Gln | Pro | Val | Gly | Glu |
|---|---|---|---|---|---|---|---|---|---|---|---|---|---|---|---|
| | | | | 565 | | | | | 570 | | | | | 575 | |

| Ser | Phe | Ala | Ile | Ile | His | Ala | Lys | Asp | Ala | Ala | Gly | Ala | Lys | Val | Glu |
|---|---|---|---|---|---|---|---|---|---|---|---|---|---|---|---|
| | | | 580 | | | | | 585 | | | | | 590 | | |

| Ser | Gly | Ala | Asn | Val | Ser | Leu | Asp | Tyr | Phe | Gly | Asn | Ala | Val | Met | Pro |
|---|---|---|---|---|---|---|---|---|---|---|---|---|---|---|---|
| | | 595 | | | | | 600 | | | | | 605 | | | |

| Tyr | Thr | Ser | Pro | Tyr | Glu | Ile | Asn | Tyr | Ile | Gly | Ile | Asn | Pro | Ser | Asp |
|---|---|---|---|---|---|---|---|---|---|---|---|---|---|---|---|
| | 610 | | | | | 615 | | | | | 620 | | | | |

| Ala | Glu | Ala | Asn | Val | Glu | Phe | Glu | Ala | Thr | Glu | Arg | Gln | Ile | Ile | Pro |
|---|---|---|---|---|---|---|---|---|---|---|---|---|---|---|---|
| 625 | | | | | 630 | | | | | 635 | | | | | 640 |

| Arg | Ala | Asn | Ser | Ile | Ser | Leu | Val | Asp | Phe | Arg | Thr | Gly | Lys | Asn | Thr |
|---|---|---|---|---|---|---|---|---|---|---|---|---|---|---|---|
| | | | | 645 | | | | | 650 | | | | | 655 | |

| Met | Val | Leu | Phe | Asn | Leu | Thr | Leu | Pro | Asn | Gly | Glu | Pro | Val | Pro | Met |
|---|---|---|---|---|---|---|---|---|---|---|---|---|---|---|---|
| | | | 660 | | | | | 665 | | | | | 670 | | |

| Ala | Ser | Thr | Ala | Gln | Asp | Ser | Glu | Gly | Ala | Phe | Val | Gly | Asp | Val | Val |
|---|---|---|---|---|---|---|---|---|---|---|---|---|---|---|---|
| | | 675 | | | | | 680 | | | | | 685 | | | |

| Gln | Gly | Gly | Val | Leu | Phe | Ala | Asn | Lys | Leu | Thr | Gln | Pro | Lys | Gly | Glu |
|---|---|---|---|---|---|---|---|---|---|---|---|---|---|---|---|
| | 690 | | | | | 695 | | | | | 700 | | | | |

| Leu | Ile | Val | Lys | Trp | Gly | Glu | Arg | Glu | Ser | Glu | Gln | Cys | Arg | Phe | Gln |
|---|---|---|---|---|---|---|---|---|---|---|---|---|---|---|---|
| 705 | | | | | 710 | | | | | 715 | | | | | 720 |

| Tyr | Gln | Val | Asp | Leu | Asp | Asn | Ala | Gln | Ile | Gln | Ser | His | Asp | Ile | Gln |
|---|---|---|---|---|---|---|---|---|---|---|---|---|---|---|---|
| | | | | 725 | | | | | 730 | | | | | 735 | |

| Cys | Lys | Thr | Ala | Lys |
|---|---|---|---|---|
| | | | 740 | |

(2) INFORMATION FOR SEQ ID NO:5:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Gln | Lys | Thr | Pro | Lys | Lys | Leu | Thr | Ala | Leu | Phe | His | Gln | Lys | Ser |
|---|---|---|---|---|---|---|---|---|---|---|---|---|---|---|---|
| 1 | | | | 5 | | | | | 10 | | | | | 15 | |

| Thr | Ala | Thr | Cys | Ser | Gly | Ala | Asn | Tyr | Ser | Gly | Ala | Asn | Tyr | Ser | Gly |
|---|---|---|---|---|---|---|---|---|---|---|---|---|---|---|---|
| | | | 20 | | | | | 25 | | | | | 30 | | |

| Ser | Lys | Cys | Phe | Arg | Phe | His | Arg | Leu | Ala | Leu | Leu | Ala | Cys | Val | Ala |
|---|---|---|---|---|---|---|---|---|---|---|---|---|---|---|---|
| | | | 35 | | | | | 40 | | | | | 45 | | |

| Leu | Leu | Asp | Cys | Ile | Val | Ala | Leu | Pro | Ala | Tyr | Ala | Tyr | Asp | Gly | Arg |
|---|---|---|---|---|---|---|---|---|---|---|---|---|---|---|---|
| | 50 | | | | | 55 | | | | | 60 | | | | |

| Val | Thr | Phe | Gln | Gly | Glu | Ile | Leu | Ser | Asp | Gly | Thr | Cys | Lys | Ile | Glu |
|---|---|---|---|---|---|---|---|---|---|---|---|---|---|---|---|
| 65 | | | | | 70 | | | | | 75 | | | | | 80 |

| Thr | Asp | Ser | Gln | Asn | Arg | Thr | Val | Thr | Leu | Pro | Thr | Val | Gly | Lys | Ala |
|---|---|---|---|---|---|---|---|---|---|---|---|---|---|---|---|
| | | | | 85 | | | | | 90 | | | | | 95 | |

| Asn | Leu | Ser | His | Ala | Gly | Gln | Thr | Ala | Ala | Pro | Val | Pro | Phe | Ser | Ile |
|-----|-----|-----|-----|-----|-----|-----|-----|-----|-----|-----|-----|-----|-----|-----|-----|
|     |     |     | 100 |     |     |     | 105 |     |     |     |     | 110 |     |     |     |

| Thr | Leu | Lys | Glu | Cys | Asn | Ala | Asp | Asp | Ala | Met | Lys | Ala | Asn | Leu | Leu |
|-----|-----|-----|-----|-----|-----|-----|-----|-----|-----|-----|-----|-----|-----|-----|-----|
|     |     | 115 |     |     |     | 120 |     |     |     |     | 125 |     |     |     |     |

| Phe | Lys | Gly | Gly | Asp | Asn | Thr | Thr | Gly | Gln | Ser | Tyr | Leu | Ser | Asn | Lys |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Gly | Asn | Gly | Lys | Ala | Thr | Asn | Val | Gly | Ile | Gln | Ile | Val | Lys | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asp | Gly | Ile | Gly | Thr | Pro | Ile | Lys | Val | Asp | Gly | Thr | Glu | Ala | Asn | Ser |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Glu | Lys | Ala | Pro | Asp | Thr | Gly | Lys | Ala | Gln | Asn | Gly | Thr | Val | Ile | Gln |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Pro | Arg | Phe | Gly | Tyr | Phe | Gly | Ser | Leu | Leu | Arg | His | Arg |
|-----|-----|-----|-----|-----|-----|-----|-----|-----|-----|-----|-----|-----|
|     |     | 195 |     |     |     |     | 200 |     |     |     |     | 205 |

( 2 ) INFORMATION FOR SEQ ID NO:6:

( i ) SEQUENCE CHARACTERISTICS:
        ( A ) LENGTH: 437 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Asn | Lys | Lys | Ser | Tyr | Ile | Asn | His | Tyr | Leu | Thr | Leu | Phe | Lys | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Thr | Leu | Leu | Phe | Thr | Leu | Ser | Ser | Asn | Pro | Val | Trp | Ala | Asn | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Lys | Thr | Val | Gln | Gly | Thr | Thr | Ser | Gly | Phe | Pro | Leu | Leu | Thr | Arg | Thr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Phe | Thr | Phe | Asn | Gly | Asn | Leu | Gln | Trp | Asn | Val | Ser | Ala | Leu | Gln | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ala | Tyr | Ile | Val | Ser | Ser | Gln | Ala | Arg | Asp | Asn | Leu | Asp | Thr | Val | His |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Gln | Ser | Ser | Glu | Ile | Asn | Ala | Pro | Thr | Asn | Ser | Leu | Ala | Pro | Phe |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Asn | Trp | Ile | Asn | Thr | Lys | Ser | Ala | Val | Glu | Leu | Gly | Tyr | Ser | Phe |
|-----|-----|-----|-----|-----|-----|-----|-----|-----|-----|-----|-----|-----|-----|-----|-----|
|     |     |     | 100 |     |     |     | 105 |     |     |     |     | 110 |     |     |     |

| Ala | Gly | Ile | Thr | Cys | Thr | Ser | Asn | Pro | Cys | Pro | Thr | Met | Lys | Leu | Pro |
|-----|-----|-----|-----|-----|-----|-----|-----|-----|-----|-----|-----|-----|-----|-----|-----|
|     |     |     | 115 |     |     |     | 120 |     |     |     |     | 125 |     |     |     |

| Leu | Leu | Phe | His | Pro | Asp | Leu | Thr | Asn | Leu | Thr | Pro | Pro | Gly | Lys | Lys |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Asn | Ser | Asp | Gly | Gly | Glu | Ile | Phe | Lys | Leu | His | Asn | Glu | Ser | Asn | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Gly | Val | Ser | Phe | Gln | Ile | Gly | Val | Lys | Thr | Asn | Thr | Ser | Leu | Asp | Trp |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Val | Asn | Ala | Lys | Asn | Asn | Phe | Ser | Ser | Leu | Lys | Val | Leu | Met | Val | Pro |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Phe | Asn | Ser | Ser | Asp | Lys | Ile | Ser | Leu | His | Leu | Arg | Ala | Lys | Phe | His |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Leu | Leu | Thr | Asp | Phe | Ser | Ser | Leu | Asn | Asn | Asp | Ile | Thr | Ile | Asp | Pro |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Met | Asn | Thr | Ser | Ile | Gly | Lys | Ile | Asn | Leu | Glu | Thr | Trp | Arg | Gly | Ser |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Thr | Gly | Asn | Phe | Ser | Val | Lys | Tyr | Val | Gly | Glu | Asp | Lys | Gly | Asp | Ile |
|-----|-----|-----|-----|-----|-----|-----|-----|-----|-----|-----|-----|-----|-----|-----|-----|

|     |     |     |     |     |     |     | 245 |     |     |     |     | 250 |     |     |     |     | 255 |     |     |
|-----|-----|-----|-----|-----|-----|-----|-----|-----|-----|-----|-----|-----|-----|-----|-----|-----|-----|-----|-----|

Ser Ile Phe Phe Asn Thr Pro Lys Ile Ile Leu Lys Lys Gln Gln Arg
           260                       265               270

Arg Cys Thr Leu Asn Asn Ala Pro Val Ser Pro Asn Pro Val Lys Leu
       275                   280                 285

Arg Ala Val Lys Lys Arg Glu Leu Glu Ala Gln Ser Glu Met Glu Gly
   290                   295               300

Gly Thr Phe Gln Leu Arg Val Asn Cys Asp Asn Thr Thr Tyr Asn Lys
305                  310            315              320

Ala Asn Gly Lys Trp Leu Phe Pro Val Val Lys Val Thr Phe Thr Asp
            325             330            335

Glu Asp Gly Thr Thr Asn Asn Gly Thr Asn Asp Leu Leu Arg Thr Gln
         340              345            350

Thr Gly Ser Gly Gln Ala Thr Gly Val Ser Leu Arg Ile Lys Arg Glu
      355                360           365

Asn Gly Thr Glu Thr Val Lys Tyr Gly Ala Asp Ser Ala Gln Met Gly
   370                375              380

Asn Ala Gly Gln Phe Glu Leu Arg Lys Gln Pro Ser Pro Ala Gly Gly
385                  390            395           400

Asp Gln Tyr Ala Glu Glu Thr Phe Lys Val Tyr Tyr Val Lys Asp Ser
         405              410            415

Thr Arg Gly Thr Leu Ile Glu Gly Lys Val Lys Ala Ala Ala Thr Phe
       420                 425           430

Thr Met Ser Tyr Gln
       435

( 2 ) INFORMATION FOR SEQ ID NO:7:

( i ) SEQUENCE CHARACTERISTICS:
        ( A ) LENGTH: 315 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Met Leu Ala Lys Ala Lys Tyr Arg Lys Asp Tyr Lys Gln Pro Asp Phe
1               5                 10              15

Thr Val Thr Asp Ile Tyr Leu Asp Phe Gln Leu Asp Pro Lys Asn Thr
         20              25              30

Val Val Thr Ala Thr Thr Lys Phe Gln Arg Leu Asn Asn Glu Ala Thr
       35               40              45

Ser Leu Arg Leu Asp Gly His Ser Phe Gln Phe Ser Ser Ile Lys Phe
   50                   55              60

Asn Gly Glu Pro Phe Ser Asp Tyr Gln Gln Asp Gly Glu Ser Leu Thr
65                  70            75            80

Leu Asp Leu Lys Asp Lys Ser Ala Asp Glu Phe Glu Leu Glu Ile Val
         85              90            95

Thr Phe Leu Val Pro Ala Glu Asn Thr Ser Leu Gln Gly Leu Tyr Gln
       100              105            110

Ser Gly Glu Gly Ile Cys Thr Gln Cys Glu Ala Glu Gly Phe Arg Gln
      115              120            125

Ile Thr Tyr Met Leu Asp Arg Pro Asp Val Leu Ala Arg Tyr Ile Ile
   130                 135            140

Lys Ile Thr Ala Asp Lys Thr Lys Tyr Pro Phe Leu Leu Ser Asn Gly
145                 150            155          160

```
Asn  Arg  Ile  Ala  Ser  Gly  Glu  Leu  Glu  Asp  Gly  Arg  His  Trp  Val  Glu
               165                      170                     175
Trp  Asn  Asp  Pro  Phe  Pro  Lys  Pro  Ser  Tyr  Leu  Phe  Ala  Leu  Val  Ala
               180                      185                 190
Gly  Asp  Xaa  Gly  Leu  Leu  Gln  Asp  Xaa  Phe  Ile  Thr  Lys  Ser  Gly  Arg
               195                      200                 205
Glu  Val  Ala  Leu  Glu  Leu  Tyr  Val  Asp  Arg  Gly  Asn  Leu  Asn  Arg  Ala
     210                      215                     220
Thr  Gly  Ala  Met  Glu  Ser  Leu  Lys  Lys  Ala  Met  Lys  Trp  Asp  Glu  Asp
225                      230                     235                          240
Arg  Phe  Ile  Leu  Glu  Phe  Tyr  Leu  Asp  Ile  Tyr  Met  Ile  Ala  Ala  Ala
                    245                      250                     255
Asp  Ser  Ser  Asn  Met  Gly  Ala  Met  Glu  Asn  Lys  Gly  Leu  Asn  Ile  Phe
               260                      265                     270
Asn  Ser  Lys  Leu  Val  Leu  Ala  Asn  Pro  Gln  Thr  Ala  Thr  Asp  Glu  Asp
          275                      280                     285
Tyr  Leu  Val  Ile  Glu  Ser  Val  Ile  Ala  His  Glu  Tyr  Ser  His  Asn  Trp
     290                      295                     300
Thr  Gly  Asn  Arg  Val  Thr  Arg  Arg  Asp  Gly  Phe
305                      310                     315
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTGCTGGATC CGTTTCTCTT GCATTACATT AGG        33

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTAGGAATTC GGAAGCGTTT TTTACTTTTT TTGG        34

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AACGAATTCT GCTGTTTATT AAGGCTTTAG        30

(2) INFORMATION FOR SEQ ID NO:11:

(i) SEQUENCE CHARACTERISTICS:
        (A) LENGTH: 30 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

AGCTGGATCC TTGTAGGGTG GGCGTAAGCC 30

(2) INFORMATION FOR SEQ ID NO:12:

(i) SEQUENCE CHARACTERISTICS:
(A) LENGTH: 217 amino acids
(B) TYPE: amino acid
(C) STRANDEDNESS: single
(D) TOPOLOGY: linear (xi) SEQUENCE DESCRIPTION: SEQ ID NO:12:

```
Met Glu Gln Phe Ile Met Lys Lys Thr Thr Thr Gly Ser Leu Ile Leu
1               5                   10                  15
Leu Ala Phe Ala Thr Asn Ala Ala Asp Pro Gln Val Ser Thr Glu Thr
            20                  25                  30
Ser Gly Lys Val Thr Phe Phe Gly Lys Val Val Glu Asn Thr Cys Lys
        35                  40                  45
Val Lys Thr Asp Ser Lys Asn Met Ser Val Val Leu Asn Asp Val Gly
    50                  55                  60
Lys Asn His Leu Lys Thr Lys Lys Asp Thr Ala Met Pro Thr Pro Phe
65                  70                  75                  80
Thr Ile Asn Leu Glu Asn Cys Ser Thr Thr Thr Thr Asn Asn Lys
                85                  90                  95
Pro Val Ala Thr Lys Val Gly Ala Tyr Phe Tyr Ser Trp Lys Asn Ala
                100                 105                 110
Asp Glu Asn Asn Glu Tyr Thr Leu Lys Asn Thr Lys Ser Gly Asn Asp
            115                 120                 125
Ala Ala Gln Asn Val Asn Ile Gln Thr Phe Asp Ala Asn Gly Thr Asp
        130                 135                 140
Ala Ile Glu Val Val Gly Asn Gly Thr Thr Asp Phe Thr His Ser Asn
145                 150                 155                 160
Thr Asn Asp Val Ala Thr Gln Gln Thr Val Asn Lys Asn His Ile Ser
                165                 170                 175
Gly Lys Ala Thr Ile Asn Gly Glu Asn Asn Val Lys Leu His Tyr Ile
                180                 185                 190
Ala Arg Tyr Tyr Ala Thr Ala Gln Ala Glu Ala Gly Lys Val Glu Ser
            195                 200                 205
Ser Val Asp Phe Gln Ile Ala Tyr Glu
        210                 215
```

(2) INFORMATION FOR SEQ ID NO:13:

(i) SEQUENCE CHARACTERISTICS:
(A) LENGTH: 216 amino acids
(B) TYPE: amino acid
(C) STRANDEDNESS: single
(D) TOPOLOGY: linear (xi) SEQUENCE DESCRIPTION: SEQ ID NO:13:

```
Met Glu Gln Phe Ile Met Lys Lys Thr Leu Leu Gly Ser Leu Ile Leu
1               5                   10                  15
Leu Ala Phe Ala Gly Asn Val Gln Ala Asp Ile Asn Thr Glu Thr Ser
            20                  25                  30
```

```
Gly Lys Val Thr Phe Phe Gly Lys Val Val Glu Asn Thr Cys Lys Val
         35                  40                  45

Lys Thr Glu His Lys Asn Leu Ser Val Val Leu Asn Asp Val Gly Lys
         50                  55                  60

Asn Ser Leu Ser Thr Lys Val Asn Thr Ala Met Pro Thr Pro Phe Thr
 65                  70                  75                  80

Ile Thr Leu Gln Asn Cys Asp Pro Thr Thr Ala Asn Gly Thr Ala Asn
                 85                  90                  95

Lys Ala Asn Lys Val Gly Leu Tyr Phe Tyr Ser Trp Lys Asn Val Asp
            100                 105                 110

Lys Glu Asn Asn Phe Thr Leu Lys Glu Gln Thr Thr Ala Asn Asp Tyr
            115                 120                 125

Ala Thr Asn Val Asn Ile Gln Leu Met Glu Ser Asn Gly Thr Lys Ala
        130                 135                 140

Ile Ser Val Val Gly Lys Glu Thr Glu Asp Phe Met His Thr Asn Asn
145                 150                 155                 160

Asn Gly Val Ala Leu Asn Gln Thr Pro Asn Thr His Ile Ser Gly
                165                 170                 175

Ser Thr Gln Leu Thr Gly Thr Asn Glu Leu Pro Leu His Phe Ile Ala
            180                 185                 190

Gln Tyr Tyr Ala Thr Asn Lys Ala Thr Ala Gly Lys Val Gln Ser Ser
        195                 200                 205

Val Asp Phe Gln Ile Ala Tyr Glu
        210                 215
```

( 2 ) INFORMATION FOR SEQ ID NO:14:

( i ) SEQUENCE CHARACTERISTICS:
        ( A ) LENGTH: 214 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
Met Glu Gln Phe Ile Met Lys Lys Thr Leu Leu Gly Ser Leu Ile Leu
 1               5                  10                  15

Leu Ala Phe Ala Gly Asn Val Gln Ala Asp Pro Asn Pro Glu Thr
            20                  25                  30

Lys Gly Lys Val Thr Phe Tyr Gly Lys Val Val Glu Asn Thr Cys Lys
         35                  40                  45

Val Lys Ser Gly Asn Arg Asp Met Ser Val Val Leu Asn Asp Val Gly
    50                  55                  60

Lys Ala His Leu Ser Gln Lys Gly Tyr Thr Ala Met Pro Thr Pro Phe
 65                  70                  75                  80

Thr Ile Thr Leu Glu Gly Cys Asn Ala Asn Thr Gly Thr Lys Pro Lys
                 85                  90                  95

Ala Asn Lys Val Gly Val Tyr Phe Tyr Ser Trp Asn Asn Ala Asp Lys
            100                 105                 110

Glu Asn Ser Tyr Thr Leu Lys Ser Thr Leu Thr Gly Thr Asp Lys Ala
            115                 120                 125

Asp Asn Val Asn Ile Gln Ile Phe Gln Glu Asn Gly Thr Asp Ala Ile
        130                 135                 140

Gly Val Ala Asp Lys Thr Ile Asp Asp Phe Thr His Lys Asn Asn Gly
145                 150                 155                 160

Ser Thr Asn Ser Asp Lys Pro Thr Lys Asn His Ile Ser Ser Ala Thr
                165                 170                 175
```

-continued

| | | | | | | | | | | | | | | | |
|---|---|---|---|---|---|---|---|---|---|---|---|---|---|---|---|
| Ala | Leu | Asn | Asn<br>180 | Gln | Asp | Gly | Ile | Ala<br>185 | Leu | His | Tyr | Ile | Ala<br>190 | Gln | Tyr |
| Tyr | Ala | Thr<br>195 | Gly | Met | Ala | Ser | Ala<br>200 | Gly | Lys | Gly | Pro | Thr<br>205 | Ser | Val | Asp |
| Phe | Pro<br>210 | Ile | Ala | Tyr | Glu | | | | | | | | | | |

We claim:

1. A method of vaccinating a mammal against *Haemophilus influenzae* comprising administering to the mammal an amount of *Haemophilus influenzae* serotype 1 LKP tip adhesin protein encoded by the hifE gene, effective to immunize a mammal against *Haemophilus influenzae* infection.

2. The method of claim 1 wherein the hifE gene comprises nucleotides 6955 to 8265 of SEQ ID NO.: 1.

3. An isolated DNA sequence encoding the *Haemophilus influenzae* serotype 1 LKP tip adhesin protein selected from the group consisting of:

a) nucleotides 6955 to 8265 of SEQ ID NO: 1;

b) the fully complementary strand of a); and c) DNA sequences that selectively hybridize to the nucleotides of a).

4. An isolated *Haemophilus influenzae* serotype 1 LKP tip adhesin protein comprising the amino acid sequence SEQ ID NO: 6.

* * * * *

UNITED STATES PATENT AND TRADEMARK OFFICE
CERTIFICATE OF CORRECTION

PATENT NO. : 5,643,725
DATED : July 1, 1997
INVENTOR(S) : Bruce A. Green and Charles C. Brinton It is certified that error appears in the above-identified patent and that said Letters Patent is hereby corrected as shown below: Title page, item [75], Under the heading Inventors, replace "Bruce A. Green, Pittsford, N.Y.; Charles C. Brinton, Jr., Export, Pa." with --Charles C. Brinton, Jr., Export, PA.; Bruce A. Green, Pittsford, N.Y.--.

Column 2, line 3, replace "gene" with --protein--.

Column 2, line 57, replace "influenzas" with --influenzae--.
Column 2, line 59, replace "influenzas" with --influenzae--.
Column 2, line 60, replace "Vaccines" with --vaccines--.
Column 2, line 66, replace "influenzas" with --influenzae--.
Column 3, line 1, replace "influenzas" with --influenzae--.
Column 3, line 5, replace "influenzas" with --influenzae--.
Column 3, line 8, replace "call" with --can--.
Column 3, line 43, replace dilution control" with --dilution. Control--.
Column 3, line 54, replace "107" with --$10^7$--.

Column 4, line 59, replace "P81034" with --P810384---.
Column 5, line 66, replace "open," with --open--.

Column 7, line 57, replace "C." with --C--.

UNITED STATES PATENT AND TRADEMARK OFFICE
CERTIFICATE OF CORRECTION

PATENT NO.  : 5,643,725
DATED       : July 1, 1997
INVENTOR(S) : Bruce A. Green and Charles C. Brinton It is certified that error appears in the above-identified patent and that said Letters Patent is hereby corrected as shown below:

Column 7, line 57, replace "C." with --C--.

Signed and Sealed this

Sixteenth Day of December, 1997

Attest:

BRUCE LEHMAN

Attesting Officer       Commissioner of Patents and Trademarks